United States Patent
Sazuka

(10) Patent No.: US 10,448,829 B2
(45) Date of Patent: Oct. 22, 2019

(54) BIOLOGICAL RHYTHM DISTURBANCE DEGREE CALCULATING DEVICE, BIOLOGICAL RHYTHM DISTURBANCE DEGREE CALCULATING SYSTEM, AND BIOLOGICAL RHYTHM DISTURBANCE DEGREE CALCULATING METHOD

(75) Inventor: Naoya Sazuka, Tokyo (JP)

(73) Assignee: Sony Corporation, Tokyo (JP)

( * ) Notice: Subject to any disclaimer, the term of this patent is extended or adjusted under 35 U.S.C. 154(b) by 1191 days.

(21) Appl. No.: 14/117,691

(22) PCT Filed: May 14, 2012

(86) PCT No.: PCT/JP2012/062289
§ 371 (c)(1),
(2), (4) Date: Nov. 14, 2013

(87) PCT Pub. No.: WO2012/161015
PCT Pub. Date: Nov. 29, 2012

(65) Prior Publication Data
US 2014/0194756 A1 Jul. 10, 2014

(30) Foreign Application Priority Data
May 24, 2011 (JP) ................................ 2011-115666

(51) Int. Cl.
*A61B 5/00* (2006.01)
*A61B 5/01* (2006.01)
(Continued)

(52) U.S. Cl.
CPC .............. *A61B 5/0002* (2013.01); *A61B 5/01* (2013.01); *A61B 5/024* (2013.01); *A61B 5/1118* (2013.01);
(Continued)

(58) Field of Classification Search
None
See application file for complete search history.

(56) References Cited

U.S. PATENT DOCUMENTS

| | | | |
|---|---|---|---|
| 5,649,968 A * | 7/1997 | Alt | A61N 1/36542 607/19 |
| 2003/0008912 A1* | 1/2003 | Lewy | A61K 31/40 514/419 |

(Continued)

FOREIGN PATENT DOCUMENTS

| | | |
|---|---|---|
| JP | 10-503944 | 4/1988 |
| JP | 01-297053 | 11/1989 |

(Continued)

OTHER PUBLICATIONS

Lin, Bo, Yifan Qiu, and Jose D. Pérezgonzález. "Sleep pattern disruption of flight attendants operating on the Asia-Pacific route." (2011).*

(Continued)

*Primary Examiner* — Etsub D Berhanu
*Assistant Examiner* — Jairo H Portillo
(74) *Attorney, Agent, or Firm* — Chip Law Group

(57) ABSTRACT

There is provided a biological rhythm disturbance degree calculating device, including a physiological index time series data acquiring unit which acquires time series data of a physiological index calculated from a biomedical signal of a subject, a calculation period deciding unit which decides a calculation period which is a time length corresponding to substantially a half of a cycle with which daily-life physiological index time series data calculated from the biomedical signal measured in daily life fluctuates, a calculating unit which calculates, during the calculation period, a phase shift amount between inspected physiological index time series data calculated from the biomedical signal measured during an inspection and the daily-life physiological index time
(Continued)

series data, and a disturbance degree deciding unit which decides a disturbance degree of a biological rhythm during the inspection of the subject based on the phase shift amount.

16 Claims, 33 Drawing Sheets

(51) Int. Cl.
*A61B 5/024* (2006.01)
*A61B 5/11* (2006.01)
*G16H 50/30* (2018.01)

(52) U.S. Cl.
CPC .......... *A61B 5/4857* (2013.01); *A61B 5/7282* (2013.01); *A61B 5/742* (2013.01); *G16H 50/30* (2018.01); *A61B 5/11* (2013.01)

(56) References Cited

U.S. PATENT DOCUMENTS

| | | | | |
|---|---|---|---|---|
| 2005/0177030 A1* | 8/2005 | Ponquinette | ......... | A61B 5/0002 600/300 |
| 2008/0114219 A1* | 5/2008 | Zhang | ................ | A61B 5/02055 600/301 |
| 2009/0099785 A1* | 4/2009 | Yamamoto | .............. | G06F 3/011 702/19 |
| 2010/0079294 A1* | 4/2010 | Rai | .......................... | A61B 5/18 340/575 |
| 2010/0112620 A1* | 5/2010 | Hayakawa | ........... | G01N 33/573 435/18 |
| 2010/0125215 A1* | 5/2010 | Kuo | ..................... | A61B 5/0006 600/509 |
| 2010/0138379 A1 | 6/2010 | Mott et al. | | |
| 2010/0268041 A1* | 10/2010 | Kraemer | .............. | A61B 5/0537 600/301 |
| 2011/0071873 A1* | 3/2011 | Vaughan | ................ | G06Q 10/06 705/7.28 |

FOREIGN PATENT DOCUMENTS

| | | |
|---|---|---|
| JP | 06-189914 | 7/1994 |
| JP | 2005-261737 | 9/2005 |
| JP | 2010-091359 | 4/2010 |

OTHER PUBLICATIONS

Tompkins, Olga S. "Business Traveler Fitness." Aaohn Journal56.6 (2008): 272-272. (Year: 2008).*

Nagano et al., An abrupt shift in the day/night cycle causes desynchrony in the mammalian circadian center. J Neurosci. Jul. 9, 2003;23(14):6141-51.

* cited by examiner

FIG. 2
21 YEARS OLD
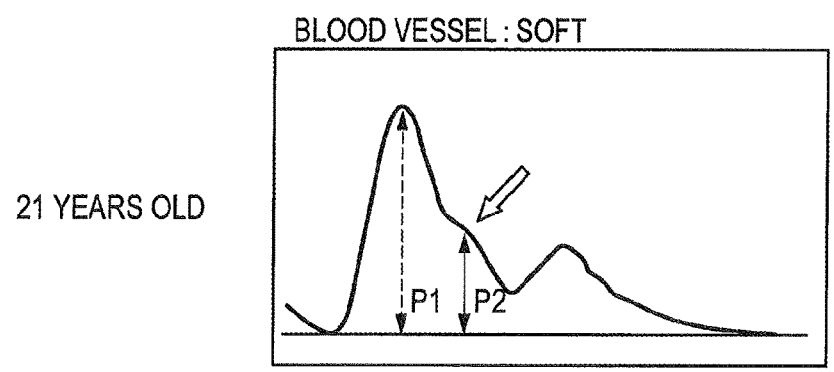
48 YEARS OLD
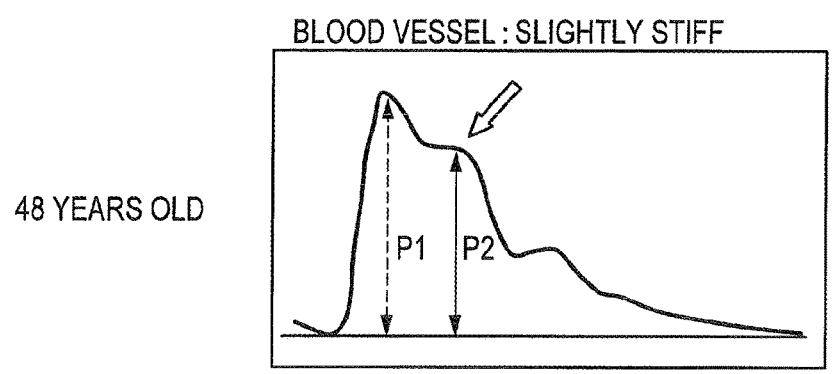
86 YEARS OLD
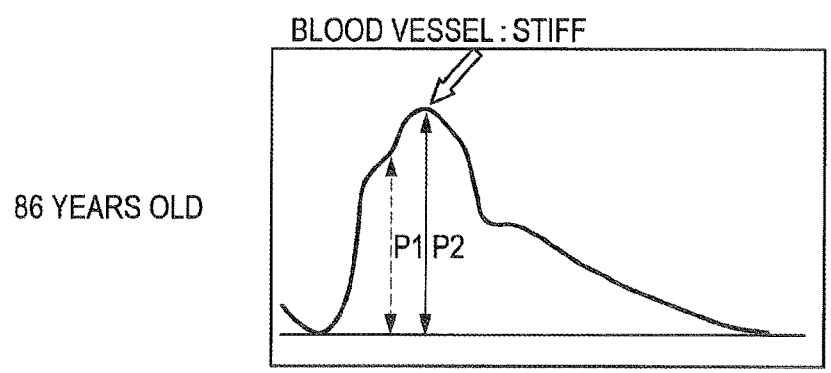

PLEASE INPUT PRIOR INFORMATION

PLEASE SELECT A CAUSE OF RHYTHM
DISTURBANCE

| |
|---|
| TRAVEL ACROSS ZONES WITH A TIME DIFFERENCE (WESTWARD) |
| TRAVEL ACROSS ZONES WITH A TIME DIFFERENCE (EASTWARD) |
| SHIFT WORK |
| IRREGULAR SLEEP |

PLEASE INPUT TIME SHIFT

HOUR

FIG. 10
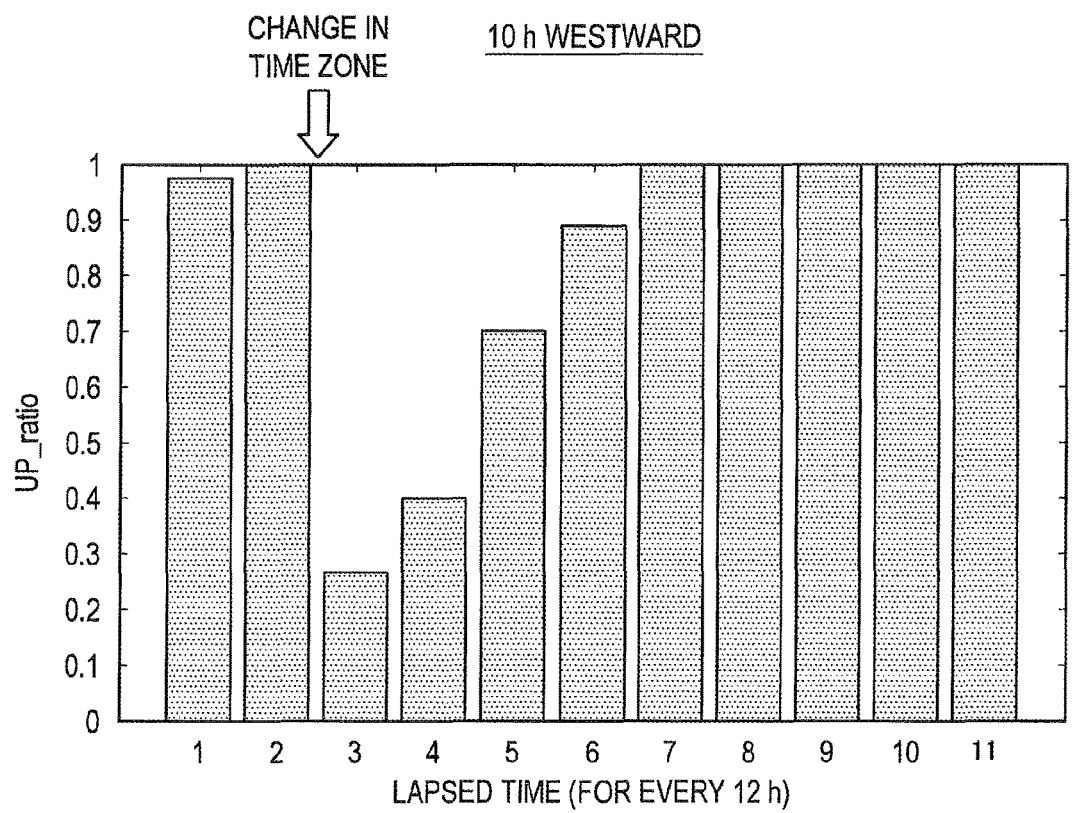
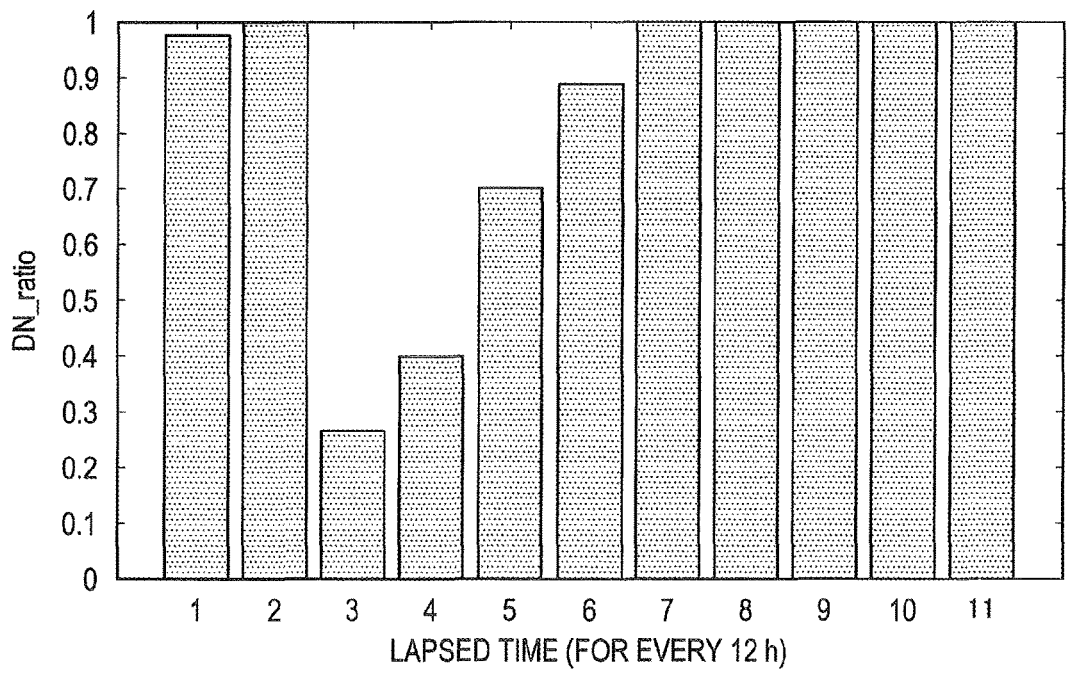

FIG. 11
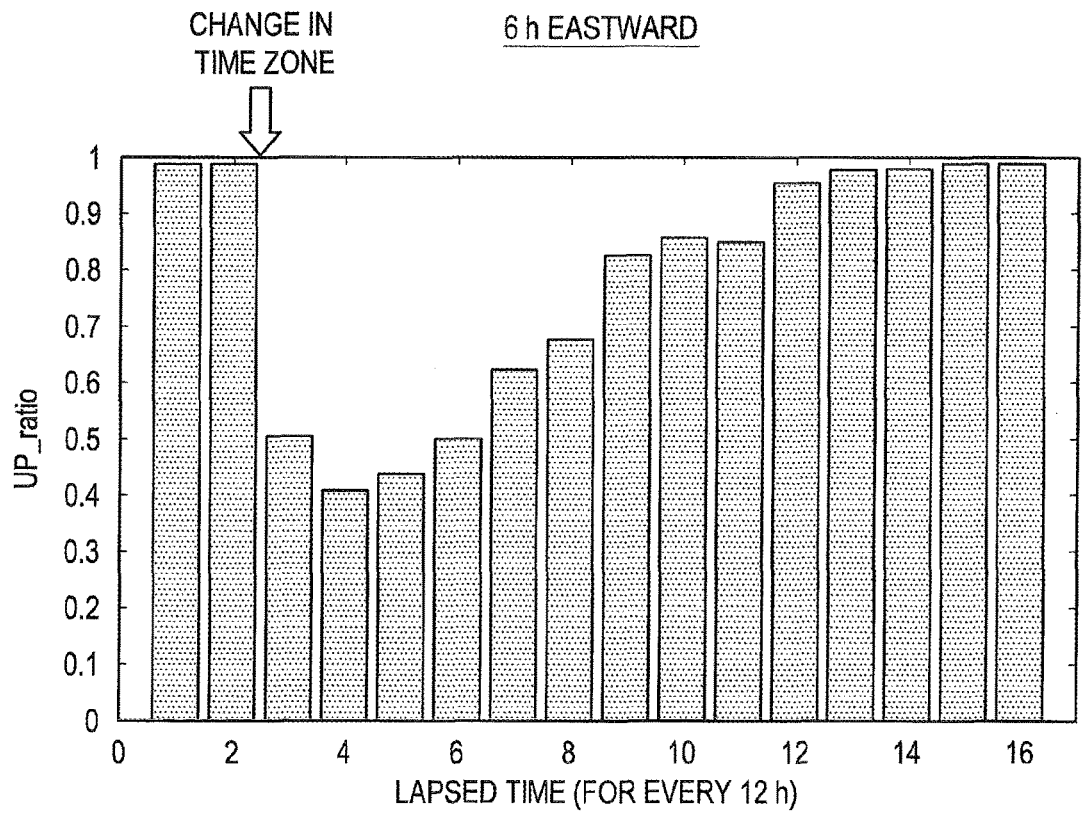
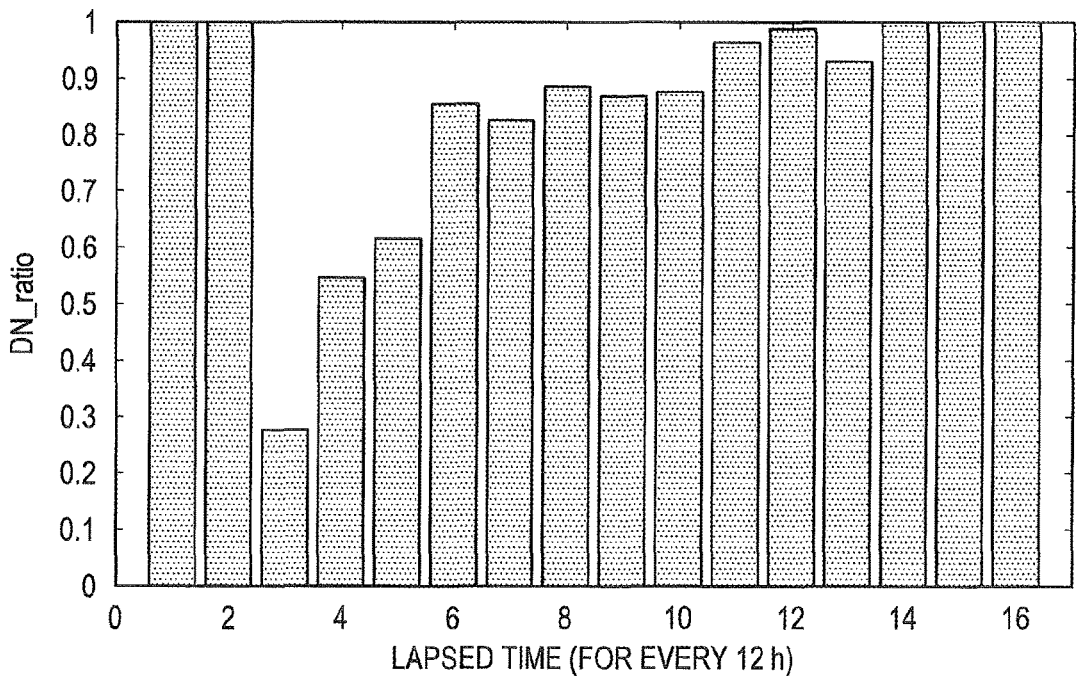

22

| CAUSE OF DISTURBANCE | TIME SHIFT | LAPSED TIME | DISTURBANCE DEGREE R |
|---|---|---|---|
| TRAVEL ACROSS ZONES WITH A TIME DIFFERENCE (Advance) | 6 h | 0.5 DAY | 0.25 |
| TRAVEL ACROSS ZONES WITH A TIME DIFFERENCE (Advance) | 6 h | 1 DAY | 0.4 |
| TRAVEL ACROSS ZONES WITH A TIME DIFFERENCE (Advance) | 6 h | 1.5 DAYS | 0.6 |
| TRAVEL ACROSS ZONES WITH A TIME DIFFERENCE (Advance) | 6 h | 2 DAYS | 0.7 |
| SHIFT WORK | 7 h | 1 DAY | 0.6 |
| SHIFT WORK | 7 h | 1.5 DAYS | 0.7 |
| SHIFT WORK | 7 h | 2 DAYS | 0.85 |
| ⋮ | ⋮ | ⋮ | ⋮ |

52

| USER ID | CAUSE OF DISTURBANCE | TIME SHIFT | LAPSED TIME | DISTURBANCE DEGREE R |
|---|---|---|---|---|
| 0000001 | TRAVEL ACROSS ZONES WITH A TIME DIFFERENCE (Advance) | 6 h | 1 DAY | 0.25 |
| 0000001 | TRAVEL ACROSS ZONES WITH A TIME DIFFERENCE (Advance) | 6 h | 1.5 DAYS | 0.4 |
| ⋮ | ⋮ | ⋮ | ⋮ | ⋮ |
| 0000002 | SHIFT WORK | 7 h | 1 DAY | 0.6 |
| 0000002 | SHIFT WORK | 7 h | 1.5 DAYS | 0.65 |
| 0000002 | SHIFT WORK | 7 h | 2 DAYS | 0.7 |
| ⋮ | ⋮ | ⋮ | ⋮ | ⋮ |

| USER ID | AVERAGE VALUE M | FIRST REFERENCE TIME POINT $t_B$ | SECOND REFERENCE TIME POINT $t_E$ |
|---|---|---|---|
| 0000001 | 36.5 | 10:00 | 22:00 |
| 0000002 | 36.3 | 9:50 | 21:50 |
| 0000003 | 37.1 | 9:30 | 21:30 |
| 0000004 | 36.7 | 9:00 | 21:00 |
| 0000005 | 35.9 | 9:15 | 21:15 |
| ⋮ | ⋮ | ⋮ | ⋮ |

FIG. 22

54b ($t_B$ 10:00 $t_E$ 22:00 FIXED)

| USER ID | AVERAGE VALUE M | UP_ratio | DN_ratio | PHYSIOLOGICAL INDEX AT TIME $t_B$ |
|---|---|---|---|---|
| 0000001 | 36.5 | 0.99 | 0.98 | POSITIVE |
| 0000002 | 36.3 | 0.92 | 0.94 | POSITIVE |
| 0000003 | 37.1 | 0.93 | 0.95 | NEGATIVE |
| 0000004 | 36.7 | 0.97 | 0.99 | POSITIVE |
| 0000005 | 35.9 | 0.98 | 0.94 | NEGATIVE |
| ⋮ | ⋮ | ⋮ | ⋮ | ⋮ |

| USER TYPE | NUMBER OF USERS (PEOPLE) | AVERAGE VALUE (°C) | AMPLITUDE (°C) | TIME POINT AT MAXIMUM VALUE | TIME POINT AT MINIMUM VALUE |
|---|---|---|---|---|---|
| MORNING TYPE | 100 | 36.5 | 1.8 | 15:30 | 03:30 |
| NIGHT TYPE | 80 | ... | ... | ... | ... |

AVERAGE BEHAVIOR OF EACH TYPE

INFORMATION ON YOU

| USER TYPE | AVERAGE TYPE |
|---|---|
| WHAT IS CAUSE OF DISTURBANCE? | TRAVEL ACROSS ZONES WITH A TIME DIFFERENCE (WESTWARD) ▽ |
| TIME SHIFT ? | 10 |

PLEASE SELECT

PLEASE INPUT

RECOVERY RATE IS

ABOUT 75 % AFTER 3.5 DAYS SINCE RHYTHM IS SHIFTED

RECOVERED IN ABOUT FIVE DAYS

BIOLOGICAL RHYTHM DISTURBANCE DEGREE CALCULATING DEVICE, BIOLOGICAL RHYTHM DISTURBANCE DEGREE CALCULATING SYSTEM, AND BIOLOGICAL RHYTHM DISTURBANCE DEGREE CALCULATING METHOD

CROSS-REFERENCES TO RELATED APPLICATIONS

The present application is the National Stage of International Application No. PCT/JP2012/062289, filed in the Japanese Patent Office as a Receiving Office on May 14, 2012, titled "DISTURBANCE DEGREE CALCULATION DEVICE FOR BIOMETRIC RHYTHM, DISTURBANCE DEGREE CALCULATION SYSTEM FOR BIOMETRIC RHYTHM, DISTURBANCE DEGREE CALCULATION METHOD FOR BIOMETRIC RHYTHM, PROGRAM, AND RECORDING MEDIUM," which claims the priority benefit to Japanese Patent Application No. 2011-115666, filed in the Japanese Patent Office on May 24, 2011, titled "DISTURBANCE DEGREE CALCULATION DEVICE FOR BIOMETRIC RHYTHM, DISTURBANCE DEGREE CALCULATION SYSTEM FOR BIOMETRIC RHYTHM, DISTURBANCE DEGREE CALCULATION METHOD FOR BIOMETRIC RHYTHM, PROGRAM, AND RECORDING MEDIUM." Each of these applications is hereby incorporated by reference in its entirety.

TECHNICAL FIELD

The present disclosure relates to a biological rhythm disturbance degree calculating device, a biological rhythm disturbance degree calculating system, a biological rhythm disturbance degree calculating method, a program, and a recording medium.

BACKGROUND ART

Various parameters related to a living body fluctuate according to a rhythm with a specific cycle called biological rhythm. A typical example of a technique which analyzes the biological rhythm is the CONSINOR method disclosed in Non-Patent Literature 1. The CONSINOR method applies time series data to a cosine curve using a least square technique, and sets a cycle, amplitude, and level of the cosine curve as characteristics of the biological rhythm. The CONSINOR method is an effective analytic method, when the time series data exhibits sinusoidal changes.

The disturbance of the biological rhythm is said to have a crucial impact on health conditions of a living body. For this reason, studies on what kind of disorders the disturbance of the biological rhythm exerts on the body have been conducted (for example, Non-Patent Literature 2). In Non-Patent Literature 2, effects of the disturbance of the biological rhythm on the body are investigated by examining a piece of tissue of a portion called suprachiasmatic nucleus (SCN: SupraChiasmatic Nucleus) of the brain of a mouse.

CITATION LIST

Non-Patent Literature

Non-Patent Literature 1: Chronobiology Encyclopedia (Asakura Shoten), Norio Ishida, Kenichi Honma Non-Patent Literature 2: Nagano, M. et al. (2003). An abrupt Shift in the Day/Night Cycle Causes Desynchrony in the Mammalian Circadian Rhythm, Journal of Neuroscience 23:6141-6151

SUMMARY OF INVENTION

Technical Problem

However, in the method of Non-Patent Literature 2, only qualitative information on the disturbance of the biological rhythm can be obtained. Further, when the biological rhythm is disturbed, a fluctuation cycle and amplitude also change and time series data of physiology indices do not exhibit sinusoidal fluctuations in many cases. Therefore, the analytic method that assumes constant fluctuations such as the CONSINOR method described above cannot be used if the biological rhythm is disturbed.

Therefore, in the present disclosure, a biological rhythm disturbance degree calculating device, a biological rhythm disturbance degree calculating system, a biological rhythm disturbance degree calculating method, a program, and a recording medium which can quantitatively evaluate a disturbance degree of a biological rhythm are proposed.

Solution to Problems

According to the present disclosure, there is provided a biological rhythm disturbance degree calculating device, including a physiological index time series data acquiring unit which acquires time series data of a physiological index calculated from a biomedical signal of a subject, a calculation period deciding unit which decides a calculation period which is a time length corresponding to substantially a half of a cycle with which daily-life physiological index time series data calculated from the biomedical signal measured in daily life fluctuates, a calculating unit which calculates, during the calculation period, a phase shift amount between inspected physiological index time series data calculated from the biomedical signal measured during an inspection and the daily-life physiological index time series data, and a disturbance degree deciding unit which decides a disturbance degree of a biological rhythm during the inspection of the subject based on the phase shift amount.

Further, according to the present disclosure, there is provided a classifying device including an information acquiring unit which acquires an average value of time series data of a physiological index calculated from a daily life biomedical signal with respect to a plurality of subjects, and a first reference time point and a second reference time point based on the average value, and a classifying unit which classifies a biological rhythm of a specific subject into any one type among a morning type, a night type, and an average type, based on information acquired by the information acquiring unit.

Further, according to the present disclosure, there is provided a biological rhythm disturbance degree calculating system including a user device including an estimation condition input unit, to which estimation conditions including a time shift of an activity time zone, and a cause of a shift of the activity time zone are input, and a transmitting unit which transmits the estimation conditions to a server, and the server including an acquiring unit which acquires a disturbance degree of a biological rhythm with respect to a plurality of subjects, the disturbance degree of the biological rhythm being calculated based on a phase shift amount between inspected physiological index time series data calculated from a biomedical signal of a subject and daily life physiological index time series data, during a calculation period which is a time length corresponding to substantially a half of a cycle with which daily-life physiological index time series data calculated from the biomedical signal measured in daily life fluctuates, an estimating unit which estimates the disturbance degree under the estimation conditions using the disturbance degrees with respect to the plurality of subjects, and a display screen generating unit which generates a display screen including information on the estimated disturbance degree and which provides the user device with the display screen.

Further, according to the present disclosure, there is provided a biological rhythm disturbance degree calculating method, including acquiring physiological index time series data calculated from a biomedical signal of a subject, deciding a calculation period having a time length which is substantially a half of a cycle with which daily-life physiological index time series data calculated from the biomedical signal measured in daily life fluctuates, calculating, during the calculation period, a phase shift amount between inspected physiological index time series data calculated from the biomedical signal measured during an inspection and the daily-life physiological index time series data, and deciding a disturbance degree of a biological rhythm during the inspection of the subject based on the phase shift amount.

Further, according to the present disclosure, there is provided a program causing a computer to execute a biological rhythm calculating method including acquiring physiological index time series data calculated from a biomedical signal of a subject, deciding a calculation period having a time length which is substantially a half of a cycle with which daily-life physiological index time series data calculated from the biomedical signal measured in daily life fluctuates, calculating, during the calculation period, a phase shift amount between inspected physiological index time series data calculated from the biomedical signal measured during an inspection and the daily-life physiological index time series data, and deciding a disturbance degree of a biological rhythm during the inspection of the subject based on the phase shift amount.

Further, according to the present disclosure, there is provided a computer-readable recording medium storing a program which causes a computer to execute a biological rhythm disturbance degree calculating method including acquiring physiological index time series data calculated from a biomedical signal of a subject, deciding a calculation period having a time length which is substantially a half of a cycle with which daily-life physiological index time series data calculated from the biomedical signal measured in daily life fluctuates, calculating, during the calculation period, a phase shift amount between inspected physiological index time series data calculated from the biomedical signal measured during an inspection and the daily-life physiological index time series data, and deciding a disturbance degree of a biological rhythm during the inspection of the subject based on the phase shift amount.

Advantageous Effects of Invention

As described above, according to the present disclosure, the disturbance degree of the biological rhythm can be quantitatively evaluated.

BRIEF DESCRIPTION OF DRAWINGS

FIG. 2 is an explanatory view of a feature of the AI value.

FIG. 5 is an explanatory view of an example of a prior information input screen.

FIG. 10 is a graph illustrating an example of temporal changes in the phase shift amount due a westward travel across zones with a time difference of 10 hours, which separately illustrates the temporal changes for each type of the phase shift amount.

FIG. 11 is a graph illustrating an example of temporal changes in the phase shift amount due to an eastward travel across zones with a time difference of 6 hours, which separately illustrates the temporal change for each type of the phase shift amount.

FIG. 21 is an explanatory view illustrating an example of the reference information stored by the information collecting server.

FIG. 22 is an explanatory view illustrating another example of the reference information stored by the information collecting server.

FIG. 34 is an explanatory view illustrating another example of the screen which displays information on the disturbance degree provided in the embodiment.

DESCRIPTION OF EMBODIMENTS

Figure 1:
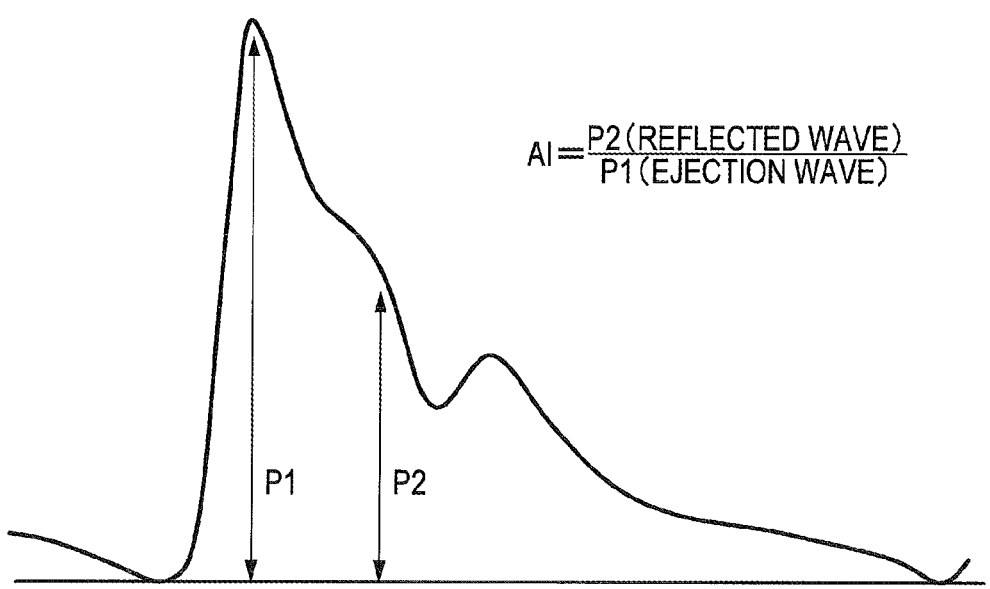
FIG. 1 is an explanatory view of an AI value calculated from a pulse wave.

Hereinafter, preferred embodiments of the present disclosure will be described in detail with reference to the appended drawings. Note that, in this specification and the drawings, elements that have substantially the same function and structure are denoted with the same reference signs, and repeated explanation is omitted.

Description shall be given in following order.
1. Overview
2. First Embodiment
2-1. Configuration
2-2. Reference information calculation processing
2-3. Disturbance degree calculation processing
2-4. Examples of effects
3. Second embodiment (example where recovery degree prediction function is provided)
3-1. Configuration
3-2. Prediction information generation processing
3-3. Examples of effects
4. Third embodiment (example of service using collected data of multiple users)
4-1. Configuration
4-2. Morning-type/night-type classification processing
4-3. Examples of effects
5. Fourth embodiment (example of system in which disturbance degree calculation is performed in server's side)
<1. Overview>

A physiological index derived from a biomedical signal fluctuates with various cycles. The rhythm of fluctuations in the physiological index is also called biological rhythm. The biological rhythm with a circadian cycle among the biological rhythms originally has a cycle of a little longer than 24 hours. The biological rhythm with a cycle of a little longer than 24 hours is usually adjusted to have a cycle of about one day due to various environmental factors, and is set to be synchronized with an external environmental rhythm. A representative environmental factor which adjusts the biological rhythm is sunlight. However, when you live irregular life style, or when you travel across zones with a dime difference, the biological rhythm significantly shifts from environmental rhythms, such as light, so that adjustment does not work well and you remain in a shifted state. Such a shift occurs between the biological rhythm and the environmental rhythm due to a travel across zones with a time difference, and a disorder which occurs in the body is called "jet-lag syndrome."

When such a shift occurs between the biological rhythm and the environmental rhythm in this manner, it is said that sleep disturbance, an increase in daytime sleepiness, performance degradation, digestive system abnormality, etc. are caused as short-term symptoms. As long-term symptoms, cancer, diabetes, overweight, etc. are caused. By continuing the life adapting to the environmental rhythm, the biological rhythm and the environmental rhythm are gradually tuned with each other. However, it is said that a tuning period varies depending on individuals, ages, and traveling directions, eastward or westward, in a case of a travel across zones with a time difference.

As for the disturbance of the biological rhythm, qualitative evaluations have been made like that the disturbance has an influence on health, and the tuning time taken until the biological rhythm is synchronized with the environmental rhythm is longer for an eastward travel than for a westward travel when the disturbance is caused due to a travel across zones with a time difference. However, each subject cannot grasp how severely the disturbance has actually occurred. Therefore, it is considered that there is a potential demand to measure a degree of disturbance. Development of the disturbance degree can be known by accumulating data of the disturbance degree. Information on both of a cause of the disturbance and a time shift between the biological rhythm and environmental rhythm may be accumulated and used to estimate the disturbance degree.

In this way, the disturbance degree which quantitatively shows the disturbance of the biological rhythm is calculated from time series data of physiological indices which are derived from biomedical signals. As the physiological indices used here, for example, core body temperatures including a tympanic membrane temperature, an oral temperature, and a rectal temperature; a pulse rate or an AI (Augmentation Index) value derived from a pulse wave; a blood pressure value; and an amount of melatonin or cortisol in blood can be enumerated. Each of these values is known to have a circadian rhythm. In order to evaluate the disturbance of the biological rhythm on an ongoing basis, a physiological index is detected continuously or periodically for a certain period. For this reason, if the core temperature detected from the inside of a mouth or tympanic membrane, a pulse wave, or the like is used, a subject does not need to undergo an invasive inspection and there is an advantage that a burden to the subject is little.

Here, the AI value is described with reference to FIGS. 1 and 2. FIG. 1 is an explanatory view of the AI value calculated from a pulse wave. FIG. 2 is an explanatory view of a feature of the AI values. The AI value is one of physiological indices which can be derived from pulse wave data. The AI value is mainly used as an index which shows arterial stiffness or a load to a heart. There are two kinds of pulse waves, including "ejection wave P1" which occurs when the heart contracts in order to send the blood throughout the whole body, and "reflected wave P2" which occurs as the ejection wave P1 is reflected from a peripheral artery or an artery branch portion when the ejection wave P1 spreads throughout the whole body. The AI value is defined as a ratio of the reflected wave P2 with respect to the ejection wave P1. When a blood vessel is stiffened, the reflected wave P2 increases and the AI value increases. As the AI value is known to change with age, for example, as illustrated in FIG. 2, the reflected wave P2 is smaller than the ejection wave P1 at the age of 21, and a difference between the ejection wave P1 and the reflected wave P2 is small at the age of 48. As shown in the example of the age of 86, the reflected wave P2 may be larger than the ejection wave P1.

In each of the following embodiments, a case where a disturbance degree for a physiological index having a circadian rhythm is calculated is described. However, various indices which change with periodicity can be used as the physiological index, and the physiological index is not limited to the following examples.

<2. First embodiment>

(2-1. Configuration)

Figure 3:
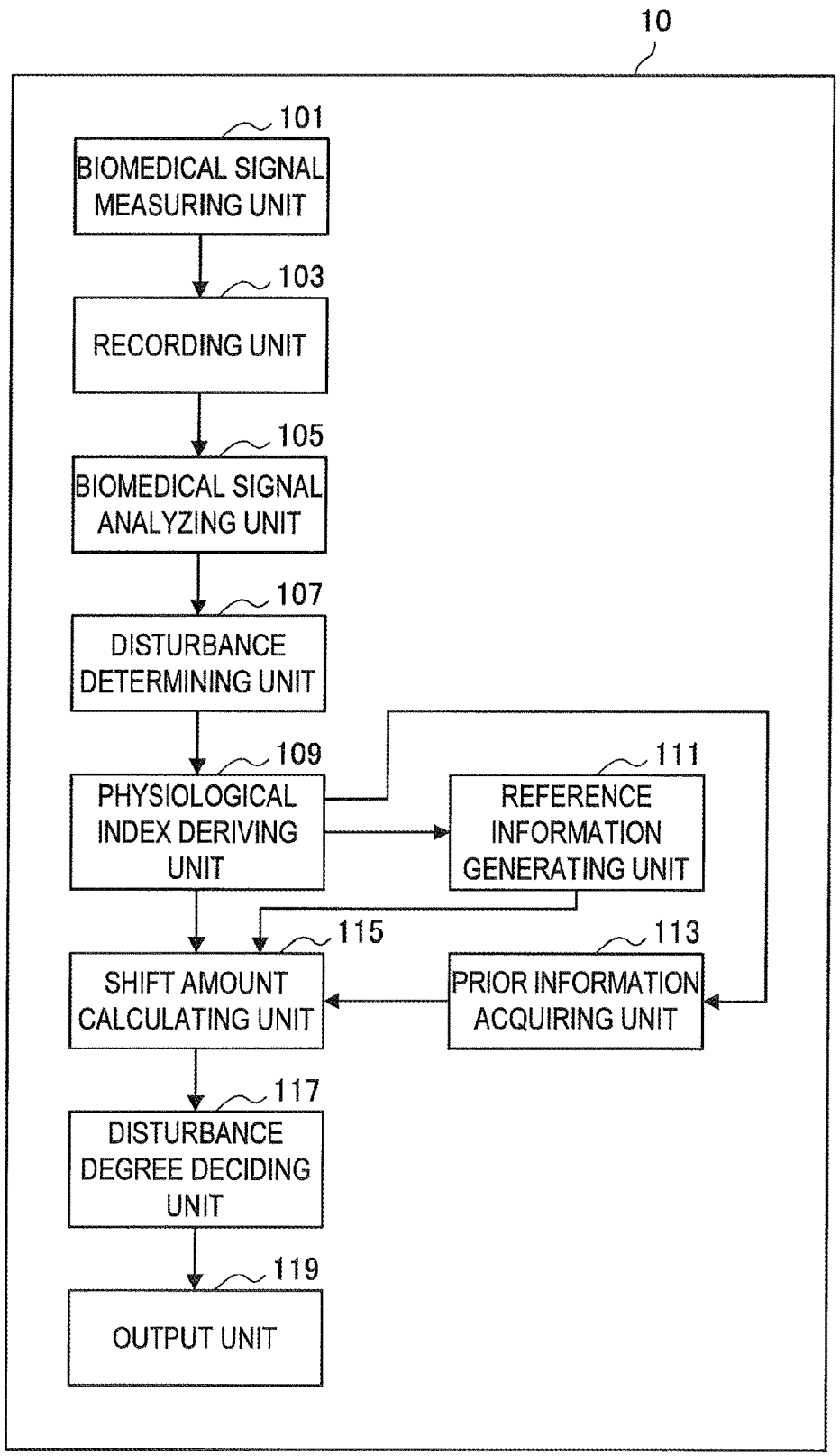
FIG. 3 is a block diagram illustrating a configuration of a biological rhythm disturbance degree calculating device according to a first embodiment of the present disclosure.
Figure 4:
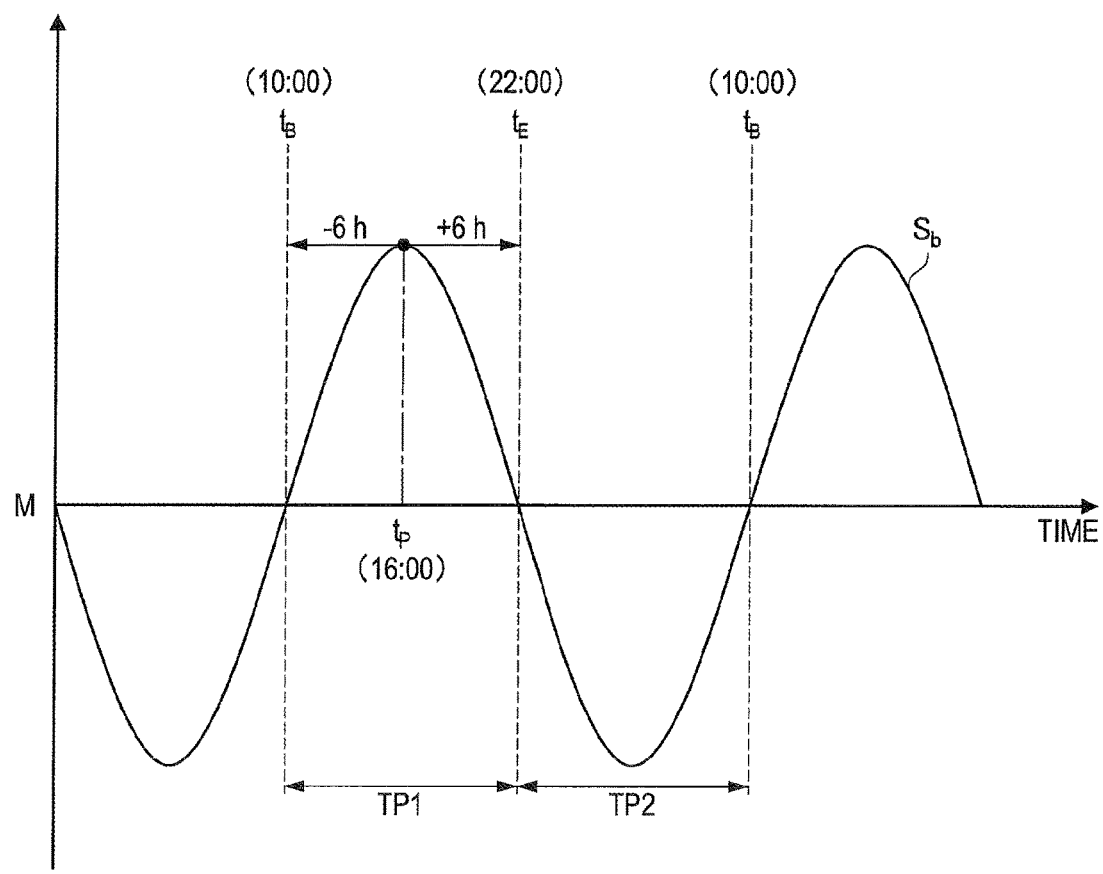
FIG. 4 is an explanatory view of reference information.
Figure 6:
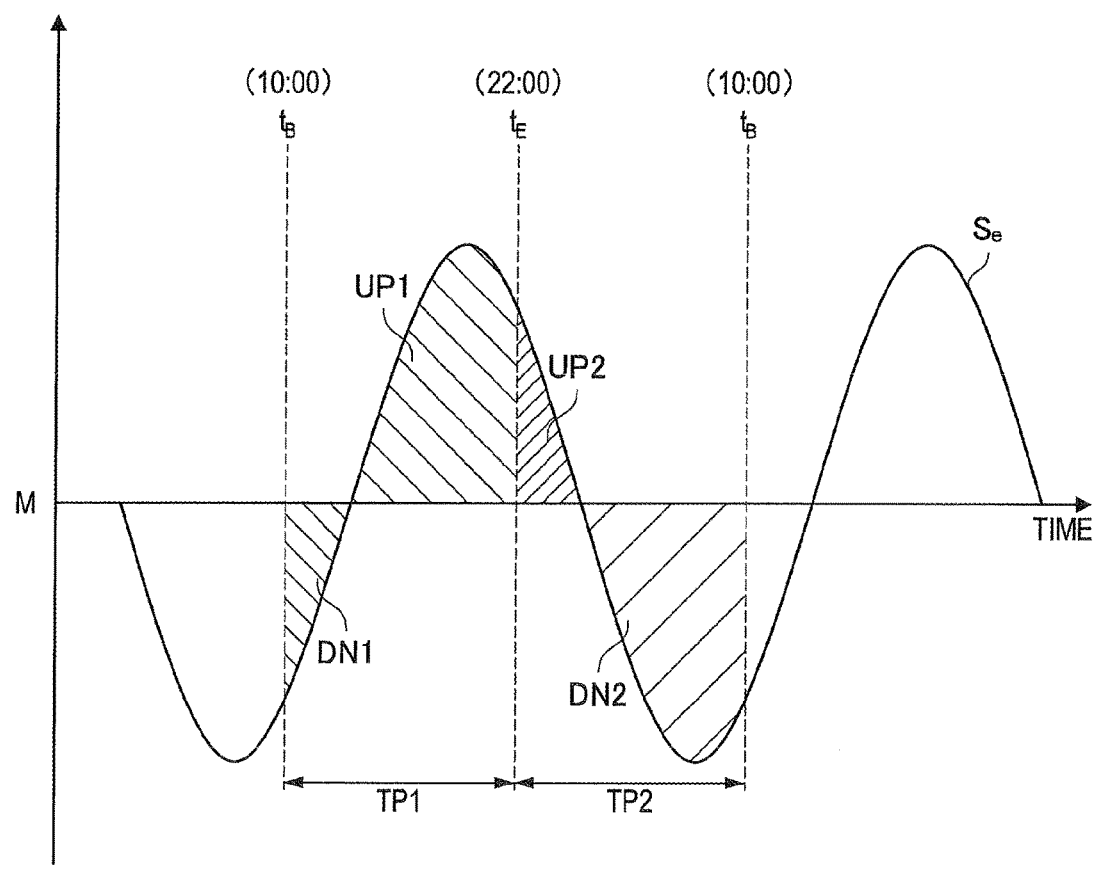
FIG. 6 is an explanatory view of an example of a phase shift amount.
Figure 8:
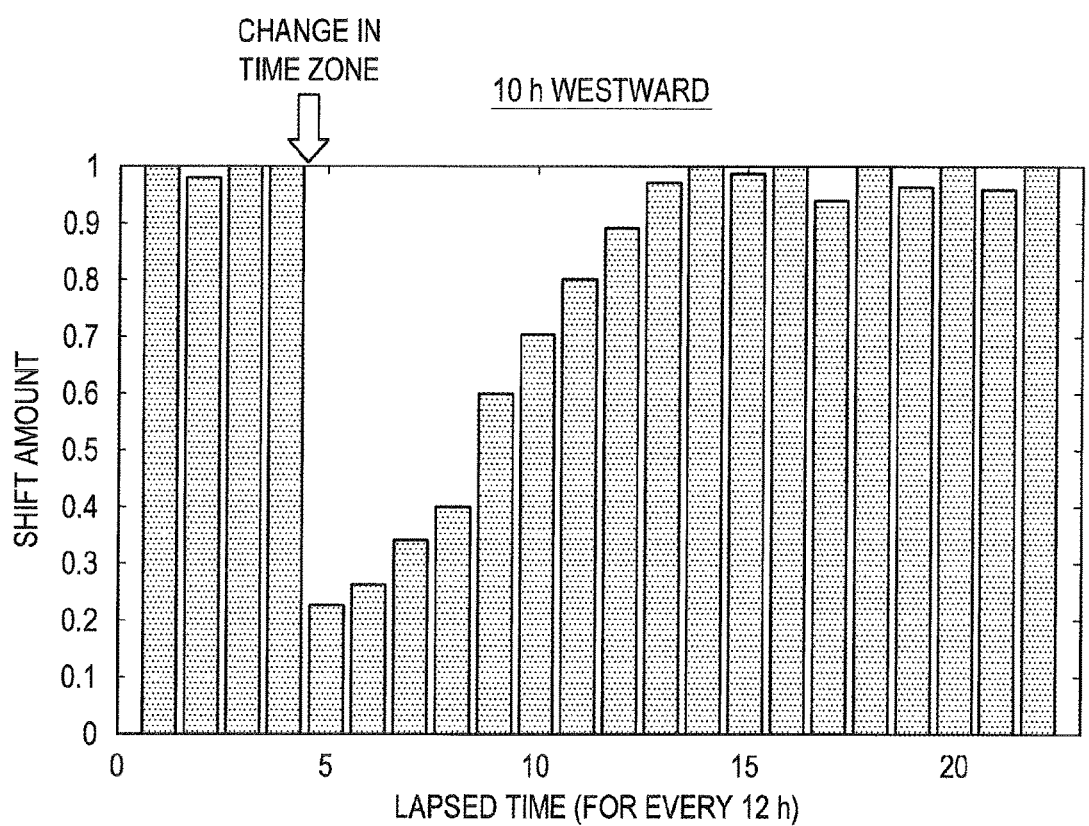
FIG. 8 is a graph illustrating an example of temporal changes in the phase shift amount due to a westward travel across zones with a time difference of 10 hours.
Figure 9:
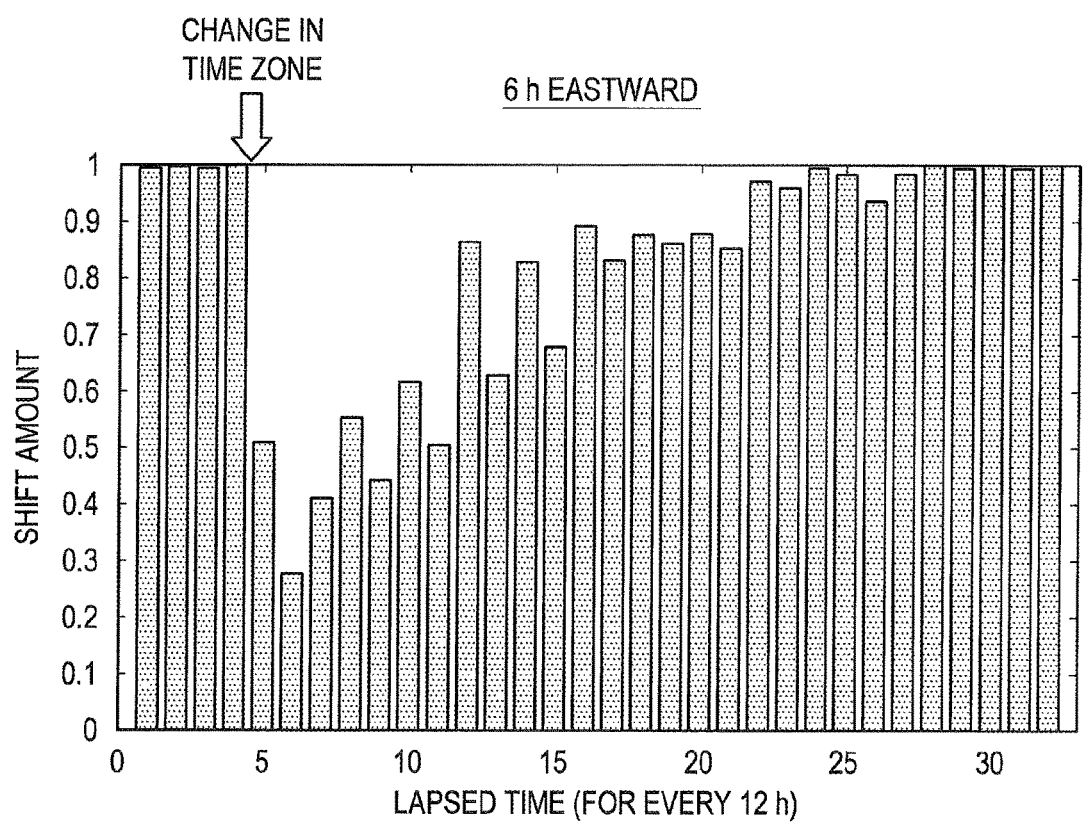
FIG. 9 is a graph illustrating an example of temporal changes in the phase shift amount due to an eastward travel across zones with a time difference of 6 hours.

Hereinafter, a configuration of a disturbance degree calculating device 10 according to a first embodiment of the present disclosure is described with reference to FIGS. 3 to 11. FIG. 3 is a block diagram illustrating the configuration of the biological rhythm disturbance degree calculating device according to the first embodiment of the present disclosure. FIG. 4 is an explanatory view of reference information. FIG. 5 is an explanatory view illustrating an example of a prior information input screen. FIG. 6 is an explanatory view with respect to a phase shift amount. FIG. 8 is a graph illustrating an example of temporal changes in the phase shift amount due to a westward travel across zones with a time difference of 10 hours. FIG. 9 is a graph illustrating an example of temporal changes in the phase shift amount due to an eastward travel across zones with a time difference of 6 hours. FIG. 10 is a graph illustrating an example of temporal changes in the phase shift amount due to a westward travel across zones with a time difference of 10 hours, which separately illustrates the temporal changes for each type of the phase shift amount. FIG. 11 is a graph illustrating an example of temporal changes in the phase shift amount due to an eastward travel across zones with a time difference of 6 hours, which separately illustrates the temporal changes for each type of the phase shift amount.

The disturbance degree calculating device 10 is an information processing apparatus having a function of calculating a disturbance degree R of a biological rhythm based on a biomedical signal of a subject. For example, the disturbance degree calculating device 10 may be an information processing apparatus such as a mobile phone, a portable music reproducing device, a portable video processing device, a portable game machine, a PC (Personal Computer), a home video processing device (a DVD recorder, a videocassette recorder, etc.), a PDA (Personal Digital Assistants), a console game machine, and electrical household appliances and electrical equipment. The disturbance degree calculating device 10 may be a server which calculates the disturbance degree R by acquiring a physiological index derived from a biomedical signal of a subject.

When referring to FIG. 1, the disturbance degree calculating device 10 includes a biomedical signal measuring unit 101, a recording unit 103, a biomedical signal analyzing unit 105, a disturbance determining unit 107, a physiological index deriving unit 109, a reference information generating unit 111, a prior information acquiring unit 113, a shift amount calculating unit 115, a biological rhythm disturbance degree deciding unit 117, and an output unit 119.

The biomedical signal measuring unit 101 has a function which measures a biomedical signal of a subject. The biomedical signal measuring unit 101 can measure a core temperature which is an example of the biomedical signal, for example. For this case, the biomedical signal measuring unit 101 may be a sensor like a thermometer which measures a core temperature, for example. The biomedical signal measuring unit 101 may measure the core temperature continuously or measure at constant intervals. For example, the biomedical signal measuring unit 101 may be a sensor which is inserted into an ear (external auditory canal) in order to measure a tympanic membrane temperature. Alternatively, the biomedical signal measuring unit 101 may be a sensor which is inserted into a mouth in order to measure an oral temperature.

Furthermore, the biomedical signal measuring unit 101 can measure a pulse wave which is an example of the biomedical signal. For this case, the biomedical signal measuring unit 101 may be a sensor which measures a pulse wave, for example, by using light or pressure. For example, the biomedical signal measuring unit 101 can measure a pulse wave from an earlobe, a fingertip, a wrist, etc. The biomedical signal measuring unit 101 is a motion sensor, such as an accelerometer, and may measure a motion of a subject's body.

Although the example where the biomedical signal measuring unit 101 is a part of the disturbance degree calculating device 10 has been described, the present technology is not limited to that example. For example, the biomedical signal measuring unit 101 may be a sensor which is a body separated from the disturbance degree calculating device 10. For this case, the biomedical signal measuring unit 101 may supply the biomedical signal to the disturbance degree calculating device 10 via a wired or wireless communication channel. When the biomedical signal measuring unit 101 is a sensor provided as a separate body from the disturbance degree calculating device 10, it is desirable for this sensor to be able to be mounted on a part of the body at which the biomedical signal is measured. For example, the sensor itself may be a wearable shape and accessories for mounting the sensor on a to-be-measured part may be used. When the biomedical signal measuring unit 101 is a part of the disturbance degree calculating device 10, it is desirable for the disturbance degree calculating device 10 itself to be mounted on a part at which a biomedical signal is to be measured. For example, the disturbance degree calculating device 10 may be a wearable shape, and accessories for mounting the disturbance degree calculating device 10 on a to-be-measured part may be used. The biomedical signal measuring unit 101 can supply the measured biomedical signal to the recording unit 103.

The recording unit 103 has a function which records the biomedical signal supplied by the biomedical signal measuring unit 101. The recording unit 103 may record the biomedical signal on a recording medium, for example, a nonvolatile memory, such as a flash memory, an MRAM (Magnetoresistive Random Access Memory), an FeRAM (Ferroelectric Random Access Memory), a PRAM (Phase change Random Access Memory), and an EEPROM (Electronically Erasable and Programmable Read Only Memory), or a magnetic recording medium, such as an HDD (Hard Disk Drive).

The biomedical signal analyzing unit 105 has a function which performs various kinds of analysis processing on the biomedical signal acquired by the biomedical signal measuring unit 101. The biomedical signal analyzing unit 105 can eliminate noise by subjecting the biomedical signal to a filter, for example.

The disturbance determining unit 107 has a function which determines whether the signal, which is input, is a biomedical signal of a subject or a disturbance, and deletes a signal determined to be the disturbance without outputting the signal as the disturbance. When the disturbance is mixed in, regardless of the disturbance of the biological rhythm, the disturbance may occur in the rhythm of a physiological index. The disturbance determining unit 107 can reduce an influence of the disturbance.

The physiological index deriving unit 109 has a function which derives a physiological index from the biomedical signal of a subject. When the biomedical signal is a core temperature, the physiological index deriving unit 109 obtains an average value of core temperatures measured for y seconds as the physiological index. At this time, desirably the value of y is about 1 to 2 minutes, for example. When the biomedical signal measuring unit 101 continuously measures the core temperature, the physiological index deriving unit 109 may divide successive data of the core temperature into data items in unit of y seconds, and may calculate the average value of the core temperatures for every y seconds. Alternatively, the physiological index deriving unit 109 may calculate the average value for y seconds, when the biomedical signal measuring unit 101 intermittently measures the core temperature at a constant interval for y seconds.

When the biomedical signal is a pulse wave, the physiological index deriving unit 109 may obtain a pulse rate or an AI value as the physiological index. When deriving the pulse rate, the physiological index deriving unit 109 extracts a peak for every waveform from the pulse wave data for y seconds first. Next, the physiological index deriving unit 109 can derive a pulse rate by counting the number of peaks within a measurement period of the y seconds and changing it into the number of peaks per minute. When deriving the AI value, the physiological index deriving unit 109 calculates a quadratic differential of one waveform of the pulse wave first. For example, the physiological index deriving unit 109 can calculate the quadratic differential by calculating a difference in the pulse wave between neighboring sampling sites or a difference between weighted values of neighboring multiple samples. Further, the physiological index deriving unit 109 extracts a point at which the quadratic differential changes from a positive value to a negative value for the second time as a reflective point. Next, the physiological index deriving unit 109 can derive the AI value by extracting a height of a peak point and a height of the reflective point for each waveform of the pulse wave, and thus by dividing the height of the reflective point by the height of the peak point.

When the biomedical signal is a motion size, the physiological index deriving unit 109 may take an amount of activity for every y seconds as the physiological index. The physiological index deriving unit 109 can derive the amount of activity by counting the number of times that an accelerometer detects subject's motion for every y seconds.

The core temperature, pulse rate, AI value, and amount of activity which are derived are stored in association with a deriving time pint at which the physiological index is derived, so that they are treated as the physiological index time series data. The physiological index deriving unit 109 may generate the physiological index time series data by associating the derived physiological index with the deriving time point at which the physiological index is derived. That is, the physiological index deriving unit 109 is an example of the physiological index time series data acquiring unit. The amount of activity may be used to estimate a time zone in which the subject is working. Alternatively, the amount of activity may be used to estimate a sleeping time of a subject. Hereinafter, the physiological index time series data which is derived from the biomedical signal in daily life is called "daily-life physiological index time series data." The physiological index time series data derived from the biomedical signal during an inspection is called "inspected physiological index time series data." The term "in daily life" means a state in which the disturbance does not appear in the biological rhythm. For example, it means a state in which a subject does not undergo a travel across zones with a time difference, shift working, and irregular life style, etc., i.e., a state in which the environmental rhythm and the biological rhythm are in sync with each other.

The reference information generating unit 111 has a function which generates reference information from the physiological index time series data during daily life and determines a calculation period during which the shift amount calculating unit 115 calculates a shift amount. That is, the reference information generating unit 111 can function as an example of the calculation period deciding unit. The reference information generating unit 111 can decide a calculation period TP between a first reference time point $t_B$ serving as a beginning time point and a second reference time point $t_E$ serving as an ending time point. Preferably, the calculation period TP is decided to be a time length which is about a half of a cycle with which the daily-life physiological index time series data fluctuates.

Hereinafter, the reference information is described with reference to FIG. 4. FIG. 4 illustrates the physiological index time series data $S_b$ in daily life. The reference information may include an average value M of the physiological index time series data $S_b$ in daily life, a first reference time point $t_B$, and a second reference time point $t_E$. The first reference time point $t_B$ is nearly a time point at which the value of the physiological index time series data $S_b$ at the time of normal conditions changes from below the average value M to above the average value M. The second reference time point $t_E$ is nearly a time point at which the value of the physiological index time series data $S_b$ at the time of normal conditions changes from above the average value M to below the average value M. A period from the first reference time point $t_B$ to the second reference time point $t_E$ is set as a first calculation period TP1, and a period from the second reference time point $t_E$ to the first reference time point $t_B$ is set as a second calculation period TP2. For example, the reference information generating unit 111 extracts a peak time point $t_P$ of the physiological index time series data $S_b$, and considers a time point 6 hours prior to the peak time point $t_P$ to be the first reference time point $t_B$. Further, the reference information generating unit 111 can consider a time point 6 hours behind the peak time point $t_P$ of the physiological index time series data $S_b$ to be the second reference time point $t_E$. The first reference time point $t_B$ and the second reference time point $t_E$ are time points at which one cycle with which the physiological index fluctuates is divided into two halves, including the first calculation period TP1 in which the physiological index in daily life is equal to or above about the average value and the second calculation period TP2 in which the physiological index in daily life is equal to or below about the average value. The physiological index used here changes with a circadian rhythm. For this reason, a time length between the first reference time point $t_B$ and the second reference time point $t_E$ may be 12 hours. Since the physiological index of a circadian rhythm is dealt here, the first reference time point $t_B$ and the second reference time point $t_E$ are determined such that same times in every day are set as reference time points when two time points are expressed in terms of time.

The prior information acquiring unit 113 has a function which acquires prior information on the cause of the disturbance in the biological rhythm. The prior information may be activity time zone information including a time shift between activity time zones of the subject who causes the disturbance of the biological rhythm and a cause of the disturbance of the activity time zone. The prior information acquiring unit 113 may acquire information which is input to the prior information input screen 71, for example, illustrated in FIG. 5 as the prior information. For example, when the cause of the disturbance of the biological rhythm is a travel across zones with a time difference, the prior information acquiring unit 113 can acquire a time difference between before and after travel (time difference between a point of departure and a point of arrival) from the information which is input to the prior information input screen 71. For this case, the prior information acquiring unit 113 may acquire information on a travel direction (westward or eastward). When the cause of the disturbance of the biological rhythm is shift work, the prior information acquiring unit 113 can acquire the shift amount of working hours which is input to the prior information input screen 71. When the cause of the disturbance of the biological rhythm is irregular sleeps, the prior information acquiring unit 113 can acquired the shift amount of sleeping hours from information which is input to the prior information input screen 71.

Further, the prior information acquiring unit 113 can estimate the prior information from the information which is detected with respect to a subject. For example, when the prior information acquiring unit 113 can acquire positional information on subject's position, the prior information acquiring unit 113 may estimate the time difference before and after travel from changes in the positional information acquired. For example, when the point of departure is Tokyo and the point of arrival is London, the prior information acquiring unit 113 assumes that the subject has traveled westward across zones with a time difference of 9 hours. Further, when the prior information acquiring unit 113 can acquire travel direction information with respect to the subject, and may estimate the shift amount of working hours for the shift work, or the shift amount of sleeping hours for the irregular sleep. For example, the prior information acquiring unit 113 may acquire an output value of the accelerometer, and may estimate the shift amount of working hours or sleeping hours.

In the determined calculation period, the shift amount calculating unit 115 has a function which calculates the inspected physiological index time series data and the daily-life physiological index time series data. Although it is possible to consider various methods of calculating a phase shift amount, the shift amount calculating unit 115 calculates the phase shift amount based on a ratio between a first characteristic quantity corresponding to the inspected physiological index time series data which has a value larger than the average value M of the daily-life physiological index time series data and a second characteristic quantity corresponding to the inspected physiological index time series data which has a value smaller than average value M. Hereinafter, regarding the phase shift amount, two specific examples are given and described.

First, an example of the phase shift amount calculated by the shift amount calculating unit 115 is described with reference to FIG. 6. FIG. 6 illustrates the physiological index time series data $S_e$ when the disturbance occurs in the biological rhythm. The shift amount calculating unit 115 can calculate the phase shift amount with respect to the physiological index time series data $S_e$ using the reference information generated by the reference information generating unit 111. In a period (first calculation period TP1 or second calculation period TP2) between the first reference time point $t_B$ and the second reference time point $t_E$, the shift amount calculating unit 115 has a function which calculates the shift amount based on a ratio of a first area UP where the value of the physiological index time series data S is larger than the average value M with respect to a second area DN where the value of the physiological index time series data is smaller than the average value M among areas surrounded by the waveform of the physiological index time series data S and the average value M. That is, the first characteristic quantity is the area UP surrounded by the waveform of the inspected physiological index time series data which has a larger value than the average value M and by a straight line showing the average value M, and the second feature quantity is the area DN of a region surrounded by the waveform of the inspected physiological index time series data which has a smaller value smaller than the average value M and by a straight line showing the average value M.

As for the physiological index time series data S, the daily-life physiological index time series data is denoted by $S_b$ and the inspected physiological index time series data is denoted by $S_e$. However, when it is not necessary to distinguish between the data items, the data is expressed as the physiological index time series data S. Further, as for the first area UP where the value of the physiological index time series data S is larger than the average value M, the value calculated for the first calculation period TP1 is expressed as a first area UP1, and the value calculated for the second calculation period TP2 is expressed as a second area UP2. However, when it is not necessary to distinguish between both of them in particular, they are collectively expressed as the first area UP. Similarly, as for the second area DN, the value calculated for the first calculation period TP1 is expressed as a second area DN1 and the value calculated for the second calculation period TP2 is expressed as a second area DN2. However, when it is not necessary to distinguish between them in particular, they are collectively expressed as the second area DN.

Hereinafter, a description about the shift amount calculated by the shift amount calculating unit 115 is concretely described. The shift amount calculating unit 115 can calculate a first shift amount UP_ratio during the period TP1 and a second shift amount DN_ratio during the period TP2. The first shift amount UP_ratio indicates a ratio of the first area UP among the areas surrounded by the waveform of the physiological index time series data S and by a straight line showing the average value M during the first calculation period TP1 which is a period from the first reference time point $t_E$ to the second reference time point $t_B$. The first shift amount UP_ratio is expressed by the following expression (1) using signs in FIG. 6. Further, the second shift amount DN_ratio indicates a ratio of the second area DN among the areas surrounded by the waveform of the physiological index time series data S and by a straight line showing the average value M during the second calculation period TP2 which is a period from the second reference time point $t_E$ to the first reference time point $t_B$. The second shift amount DN_ratio is expressed by the following expression (2) using the signs in FIG. 6.

$$\text{UP\_ratio} = \frac{UP1}{UP1 + DN1} \qquad \text{Equation (1)}$$

$$\text{DN\_ratio} = \frac{DN2}{UP2 + DN2} \qquad \text{Equation (2)}$$

Further, the shift amount calculating unit 115 can also calculate the shift amount with respect to the physiological index time series data $S_b$ in daily life. As illustrated in FIG. 4, in an ideal case where a time point at which the first reference time point $t_B$ and the reference time point $t_E$ become the average value M can be precisely extracted, both of the values of the first shift amount UP_ratio and the second shift amount DN_ratio are 1.

Figure 7:
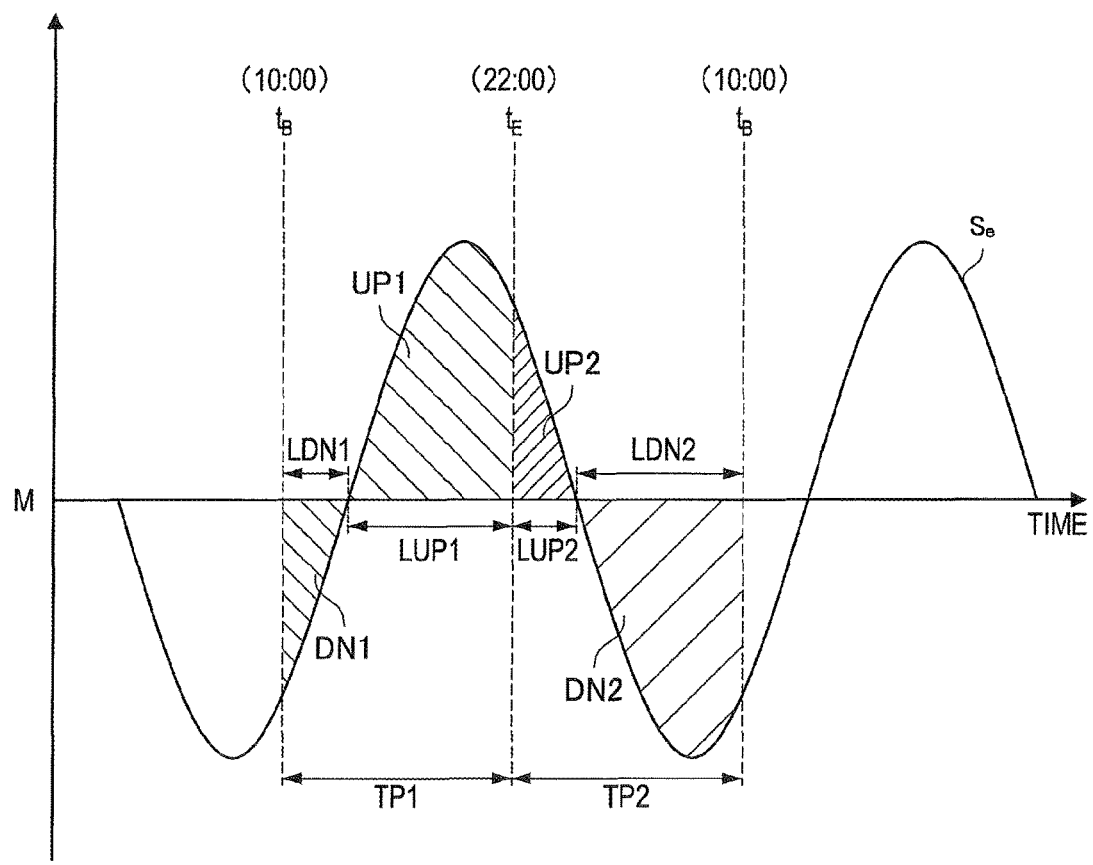
FIG. 7 is an explanatory view of another example of the phase shift amount.

Next, a description about another example of the shift amount calculated by the shift amount calculating unit 115 is made with reference to FIG. 7. The first feature quantity is a time length LUP of a period during which the inspected physiological index time series data has a value larger than the average value M, and the second feature quantity is a time length LDN of a period during which the inspected physiological index time series data takes a value smaller than the average value M. The shift amount is calculated based on a ratio between the values of the LUP and the LDN.

Hereinafter, the shift amount calculated by the shift amount calculating unit 115 is concretely described. The shift amount calculating unit 115 can calculate the first shift amount UP_ratio during the first period TP1 and the second shift amount DN_ratio during the second period TP2. The first shift amount UP_ratio indicates a ratio of a time length LUP1 of a period during which the inspected physiological index time series data has a value larger than the average value M with respect to a time length of the first calculation period TP1 which is a period from the first reference time point $t_B$ to the second reference time point $t_E$. The first shift amount UP_ratio is expressed by the following expression (3) using signs in FIG. 7. Further, the second shift amount DN_ratio indicates a ratio of a time length LDN2 of a period during which the inspected physiological index time series data has a value smaller than the average value M with respect to a time length of the second calculation period TP2 which is a period from the second reference time point $t_E$ to the first reference time point $t_B$. The second shift amount DN_ratio is expressed by the following expression (4) using signs in FIG. 7.

$$\text{UP\_ratio} = \frac{LUP1}{LUP1 + LDN1} \qquad \text{Equation (3)}$$

$$\text{DN\_ratio} = \frac{LDN2}{LUP2 + LDN2} \qquad \text{Equation (4)}$$

The disturbance degree deciding unit 117 has a function which decides the disturbance degree R of the biological rhythm during the inspection of the subject, based on the shift amount calculated by the shift amount calculating unit 115. The disturbance degree deciding unit 117 can decide any one of the first shift amount UP_ratio, the second shift amount DN_ratio, and the average value of the first shift amount UP_ratio and the second shift amount DN_ratio as the disturbance degree R. For example, the disturbance degree deciding unit 117 can set a disturbance degree R for the first calculation of period TP1 as the first shift amount UP_ratio and a disturbance degree R for the second calculation period TP2 as the second shift amount DN_ratio. Alternatively, the disturbance degree R for 24 hours which is a total of the first calculation period TP1 and the second calculation period TP2 can be the average value of the first shift amount UP_ratio and the second shift amount DN_ratio. Especially, when the cause of the shift of the activity time zone is an eastward travel across zones with a time difference, the disturbance degree deciding unit 117 may set the average value of the first shift amount UP-ratio and the second shift amount DN_ratio as the disturbance degree R. Next, this point is described with reference to FIGS. 8 to 11.

FIG. 8 illustrates an example of temporal changes in the shift amount (UP_ratio or DN_ratio) due to a westward travel across zones with a time difference of 10 hours. A horizontal axis indicates a lapsed time period. For example, when the value on the horizontal axis is 1, the first shift amount for the first calculation period TP1 of a specific day is indicated by the value on a vertical axis. When the value on the horizontal axis is 2, the second shift amount for the second calculation period TP2 which is successive to the first calculation period TP1 of the specific day is indicated by a value on the vertical axis. According to FIG. 8, the shift amount after the westward travel across time zones with a time difference dramatically decreases immediately after the travel, and then gradually approximates the value 1 which is the value in daily life, as time passes. The smaller the value of the shift amount, the larger a difference between a time point at which the value of the physiological index time series data $S_b$ becomes the average value M, and the first reference time point $t_B$ and the second reference time point $t_E$. Further, as the difference between the time point at which the value of the physiological index time series data $S_b$ becomes the average value M, and the first reference time point $t_B$ and the second reference time point $t_E$ decreases, the shift amount becomes closer to "1." For example, since the value of the shift amount is 0.7 on a sixth day after a time difference occurs, the value is recovered to about 70% on a third day after traveling across zones with a time difference.

Meanwhile, FIG. 9 illustrates an example of temporal changes in the shift amount due to an eastward traveling across zones with a time difference of 6 hours. According to FIG. 9, since the shift amount after the eastward traveling across zones with a time difference gradually approximates 1, fluctuating up and down in value.

In the graphs of FIGS. 8 and 9, the vertical axis indicates the UP_ratio or DN_ratio. These samples are divided into a portion for the first calculation period TP1 and a portion for the second calculation period TP2 and the divided results are separately illustrated in FIGS. 10 and 11. With reference to FIG. 10, as for a behavior of the temporal changes in the shift amount due to a westward travel across zones with a time difference, no difference in the behavior appears between the first calculation period TP1 and the second calculation period TP2. However, with reference to FIG. 11, as for a behavior of the temporal changes in the shift amount due to an eastward travel across zones with a time difference, a difference appears in the behavior between the first calculation period TP1 and the second calculation period TP2.

For this reason, the disturbance degree deciding unit 117 may decide the disturbance degree R using a different shift amount depending on the cause of the shift of the activity time zone. For example, it is desirable that the disturbance degree deciding unit 117 takes the average value of the value of the UP_ratio and the value of the DN_ratio as the disturbance degree R in the case of the eastward travel across zones with a time difference. Meanwhile, in the case of the westward travel across zones with a time difference, shift works, and irregular sleeping habits, the disturbance degree deciding unit 117 may take any one of the first shift amount UP_ratio, the second shift amount DN_ratio, and the average value of the first shift amount UP_ratio and the second shift amount DN_ratio as the disturbance degree R.

The output unit 119 has a function which provides the subject etc. with information, including the calculated result of the disturbance degree R. The output unit 119 may provide the calculated result of the disturbance degree R by causing a display to display a display screen generated. Alternatively, the output unit 119 may provide the calculated result of the disturbance degree R by outputting voice. When the output unit 119 provides the calculated result of the disturbance degree R using the display screen, the output unit 119 may provide the display screen including the graph illustrated in FIG. 8, for example. Alternatively, the output unit 119 may provide the display screen in which the value of a latest disturbance degree R is indicated in number at the time of output.

Hereinabove, examples of the functions of the disturbance degree calculating device 10 according to the present embodiment has been described. Each component described above may be configured using a general-purpose member or circuit, and may be configured as hardware dedicated to the function of each component. Further, the function of each component may be performed in a manner that an arithmetic unit, such as a CPU (Central Processing Unit) reads a control program, in which the processing procedure for achieving the function is described, from a recording medium, such as a ROM (Read Only Memory) or a RAM (Random Access Memory), and interprets and executes the control program. Therefore, it is possible to suitably change the configuration to be used according to skill levels whenever the present embodiment is implemented.

Further, each function of the disturbance degree calculating device 10 according to the present embodiment may be realized by a plurality of devices. For example, the sensor which acquires a biomedical signal of a subject, the device which calculates the disturbance degree R, and the device which outputs the calculated result of the disturbance degree R may be devices provided as separate bodies, respectively. A terminal device which has functions of the biomedical signal measuring unit 101, the recording unit 103, and the output unit 119 may transmit the acquired biomedical signal via a wireless communication channel to a separate server having functions of the biomedical signal analyzing unit 105, the disturbance determining unit 107, the physiological index deriving unit 109, the reference information generating unit 111, the prior information acquiring unit 113, the shift amount calculating unit 115, and the disturbance degree deciding unit 117. For this case, the server transmits an analysis result to the terminal device. The terminal device may be a portable type, wristwatch type, or stationary type. The sensor which acquires the biomedical signal may be built in the terminal device, or may be provided as a separate device. When the terminal device and the sensor are provided as separate bodies, the sensor transmits the biomedical signal acquired, via a wired communication channel or a wireless communication channel, to the terminal device. Not only the form in which each function of the server is realized by one server but also the form in which each function is realized through distributed processing using by a plurality of servers falls within the scope of the present technology.

A computer program for realizing each function of the disturbance degree calculating device 10 according to the present embodiment described above can be created and mounted to a personal computer etc. Further, a computer-readable recording medium in which the computer program is stored can be provided. The recording medium is a magnetic disk, an optical disc, a magneto-optical disc, a flash memory, or the like, for example. The computer program may be distributed, for example, via a network, without using the recording medium.

Next, an example of operation of the disturbance degree calculating device 10 is described. The operation of the disturbance degree calculating device 10 includes reference information calculation processing for acquiring reference information for every subject in advance, and disturbance degree calculation processing using the reference information. Hereinafter, each processing is described.

(2-2. Reference Information Calculation Processing)

Figure 12:
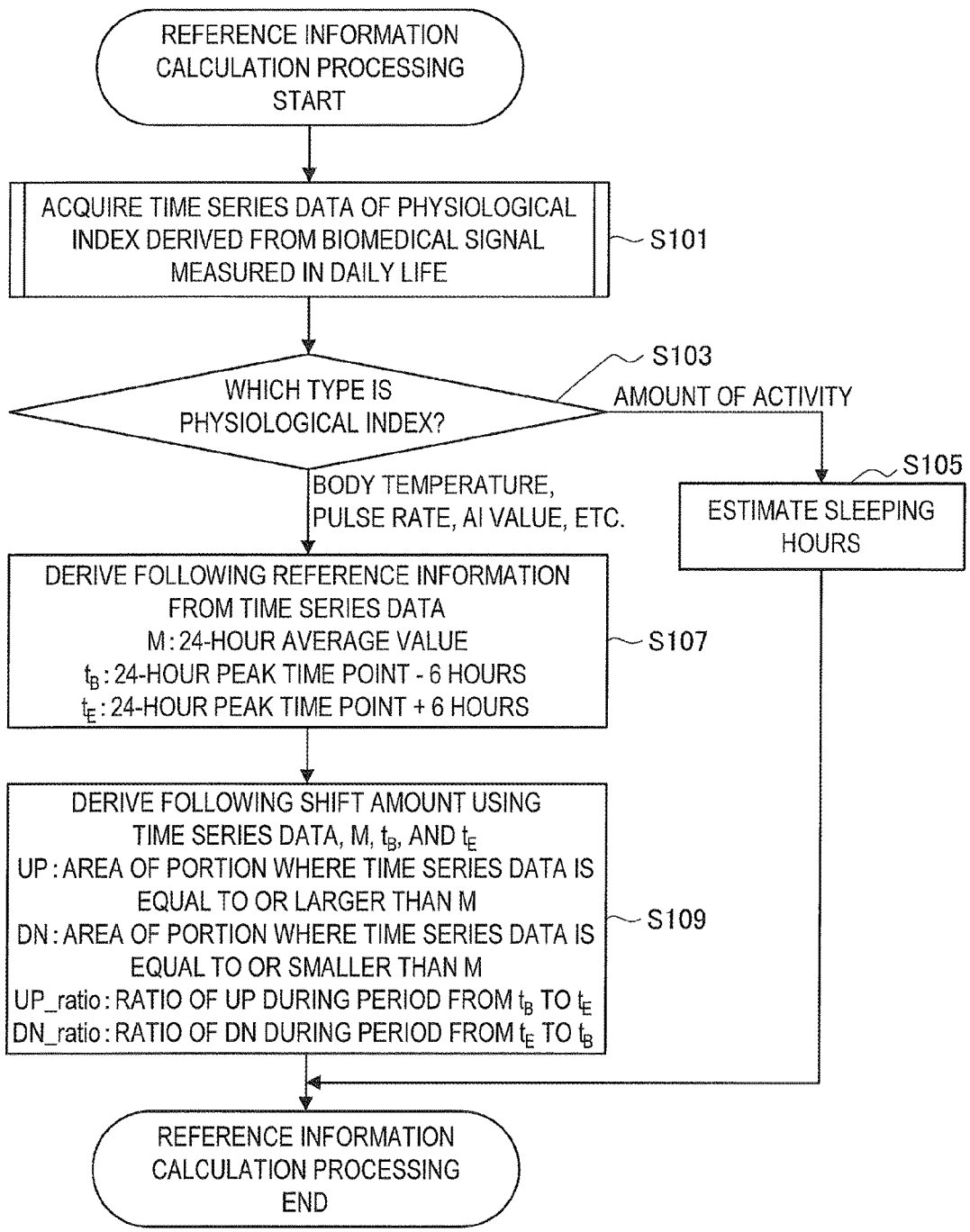
FIG. 12 is a flowchart illustrating the overall flow of reference information calculation processing.
Figure 13:
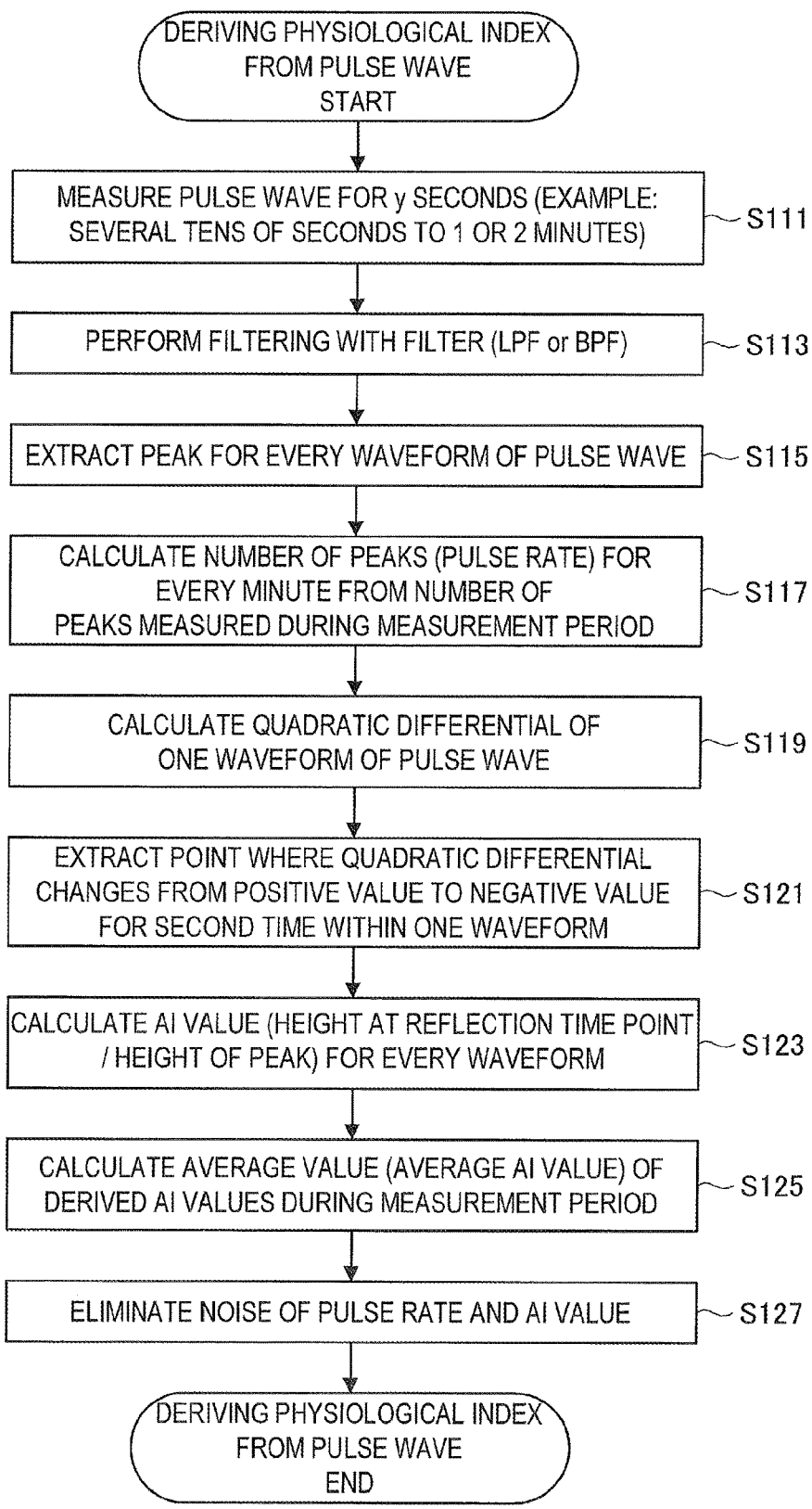
FIG. 13 is a flowchart illustrating a flow of physiological index derivation processing using a pulse wave.
Figure 14:
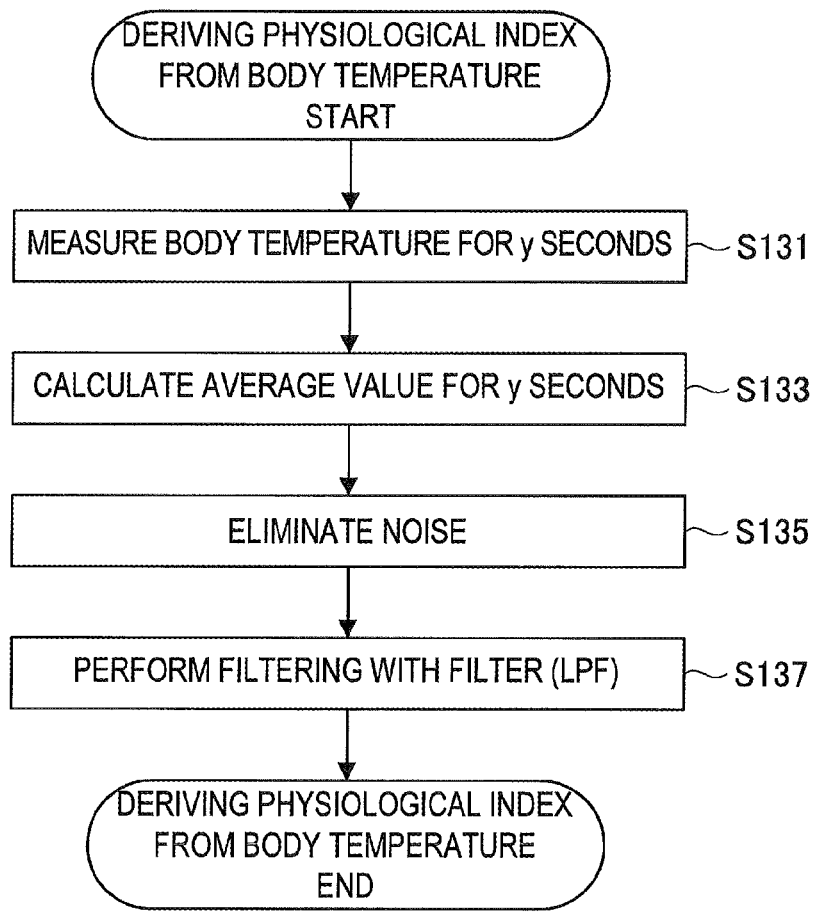
FIG. 14 is a flowchart illustrating a flow of physiological index derivation processing using a body temperature.

First, a preparation operation of preparing the reference information is described with reference to FIGS. 12 to 14. FIG. 12 is a flowchart which illustrates the overall flow of the reference information calculation processing. FIG. 13 is a flowchart which illustrates a flow of physiological index derivation processing of deriving a physiological index from a pulse wave. FIG. 14 is a flowchart which illustrates a flow of physiological index derivation processing of deriving a physiological index from a body temperature.

First, the physiological index deriving unit 109 acquires the time series data of the physiological index derived from the biomedical signal in daily life (S101). The physiological index time series data acquisition processing of Step S101 is processing of acquiring physiological index time series data by storing the physiological index derived through the physiological index derivation processing described below with reference to FIGS. 13 and 14, along an acquisition time point at which the physiological index is acquired.

Here, the kind of the physiological index in the physiological index time series data $S_b$ acquired in Step S101 is determined by the physiological index deriving unit 109 (S103). When the physiological index acquired here is an amount of activity, the reference information generating unit 111 estimates subject's sleeping hours from the physiological index time series data $S_b$ (S105). Meanwhile, when the physiological index is a core temperature, a pulse rate, an AI value, or the like, the reference information generating unit 111 then derives the average value M of the physiological index time series data $S_b$ for 24 hours, the first reference time point $t_B$, and the second reference time point $t_E$ from the physiological index time series data $S_b$ (S107). Here, the first reference time point $t_B$ is a time point 6 hours prior to a peak time point within 24 hours in the physiological index time series data $S_b$, and the second reference time point $t_E$ is a time point 6 hours behind the peak time point within 24 hours in the physiological index time series data $S_b$.

The shift amount calculating unit 115 may calculate the shift amount in daily life using the reference information which is calculated in Step S107, (S109). Here, the shift amount calculated is the first shift amount UP_ratio which is a ratio of the area UP of a portion where the value of the physiological index time series data $S_b$ is equal to or larger than the average value M during the first calculation period TP1 ranging from the first reference time point $t_B$ to the second reference time point $t_B$, or the second shift amount DN_ratio when the value of the physiological index time series data $S_b$ is equal to or smaller than the average value M for the second calculation period TP2 ranging from the second reference time point $t_E$ to the first reference time point $t_B$.

Here, with reference to FIGS. 13 and 14, a physiological index derivation process in the physiological index time series data acquisition processing in Step S101 is described. FIG. 13 illustrates an example of the physiological index derivation processing when the biomedical signal is a pulse wave. In this case, the biomedical signal measuring unit 101 measures a pulse wave for y seconds first (S111). Subsequently, the biomedical signal analyzing unit 105 extracts a signal of a desired zone by filtering the acquired biomedical signal with a filter (low pass filter LPF or band pass filter BPF) (S113). Subsequently, the physiological index deriving unit 109 extracts a peak for each waveform of a pulse wave (S115). Subsequently, the physiological index deriving unit 109 calculates the number of peaks per minute from the number of peaks for a measurement period (y seconds) as the pulse rate (S117).

Subsequently, the physiological index deriving unit 109 calculates a quadratic differential of one waveform of a pulse wave (S119). Subsequently, the physiological index deriving unit 109 extracts a time point at which the quadratic differential changes from a positive value to a negative value for the second time within one waveform as a reflective time point (S121). Subsequently, the physiological index deriving unit 109 calculates the AI value for each waveform (S123). In this case, as for the AI value, the AI value for each waveform can be calculated by dividing the height of the pulse wave at the reflective time point by the height of the pulse wave at the peak time point. In addition, the physiological index deriving unit 109 calculates the average value during a measurement period of the derived AI value and uses this value as the average AI value (S125). Subsequently, the physiological index deriving unit 109 eliminates noise in the calculated physiological indices (pulse rate and AI value) (S127).

Subsequently, an example of the physiological index derivation processing when the biomedical signal is a body temperature is illustrated in FIG. 14. For this case, the biomedical signal measuring unit 101 measures the body temperature for y seconds first (S131). Desirably, the body temperature measured at this time is a core temperature. Subsequently, the physiological index deriving unit 109 calculates the average value of the body temperatures for y seconds (S133). Subsequently, a noise elimination of eliminating the value when the average value of the temperatures for y seconds sharply changes compared with immediately preceding and subsequent temperatures (S135). Subsequently, when the noise is large, the signal is put through the filter (low pass filter LPF) again (S137).

Although not illustrated, when the biomedical signal is an amount of activity, the amount of activity for every y seconds is calculated based on the output of a motion sensor, such as an accelerometer.

(2-3. Disturbance Degree Calculation Processing)

Figure 15:
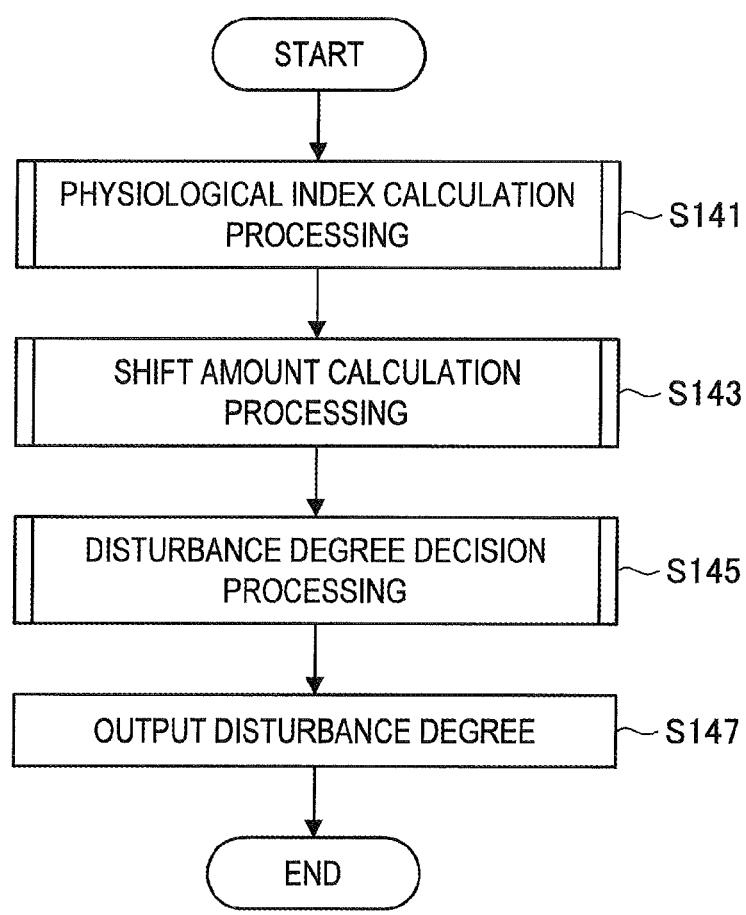
FIG. 15 is a flowchart illustrating the overall flow of disturbance degree calculation processing.
Figure 16:
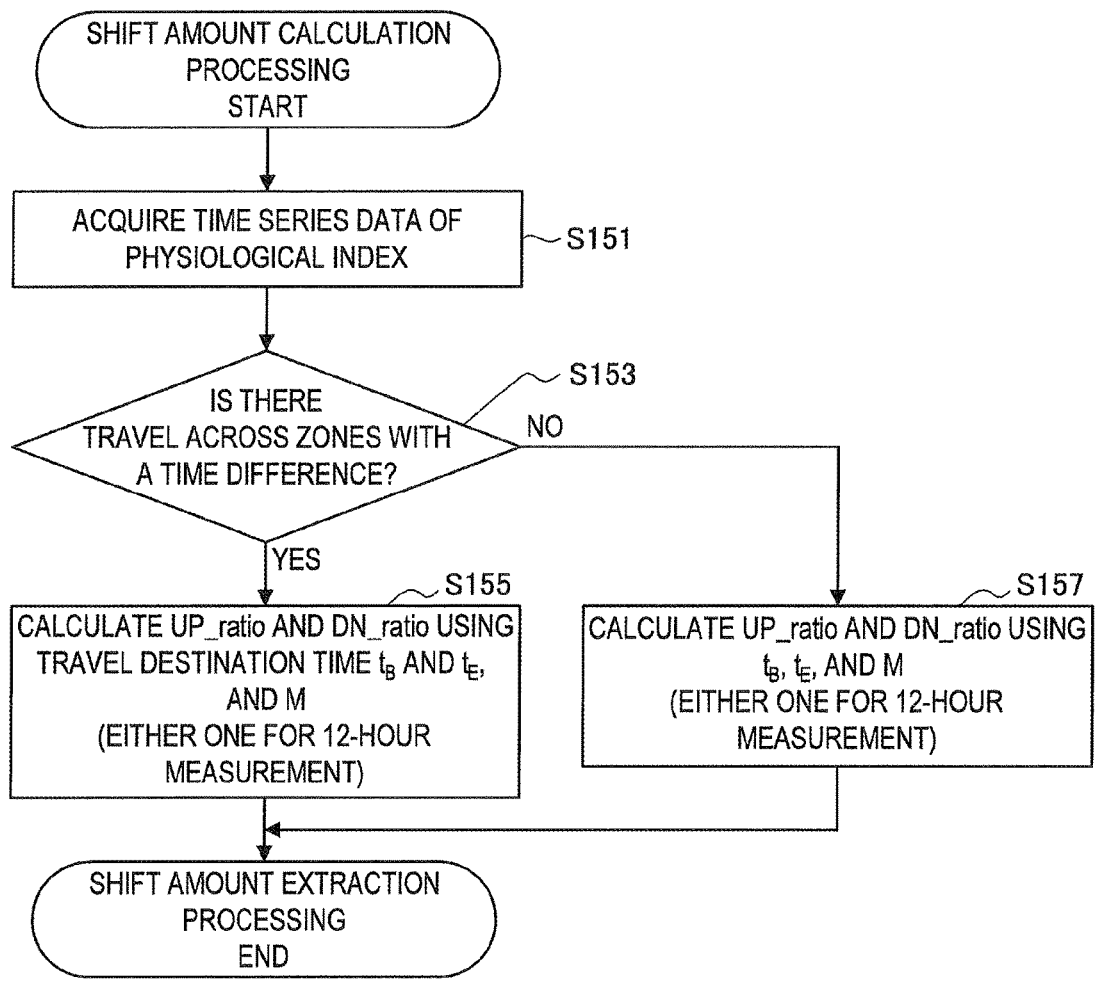
FIG. 16 is a flowchart illustrating a flow of phase shift amount extraction processing.
Figure 17:
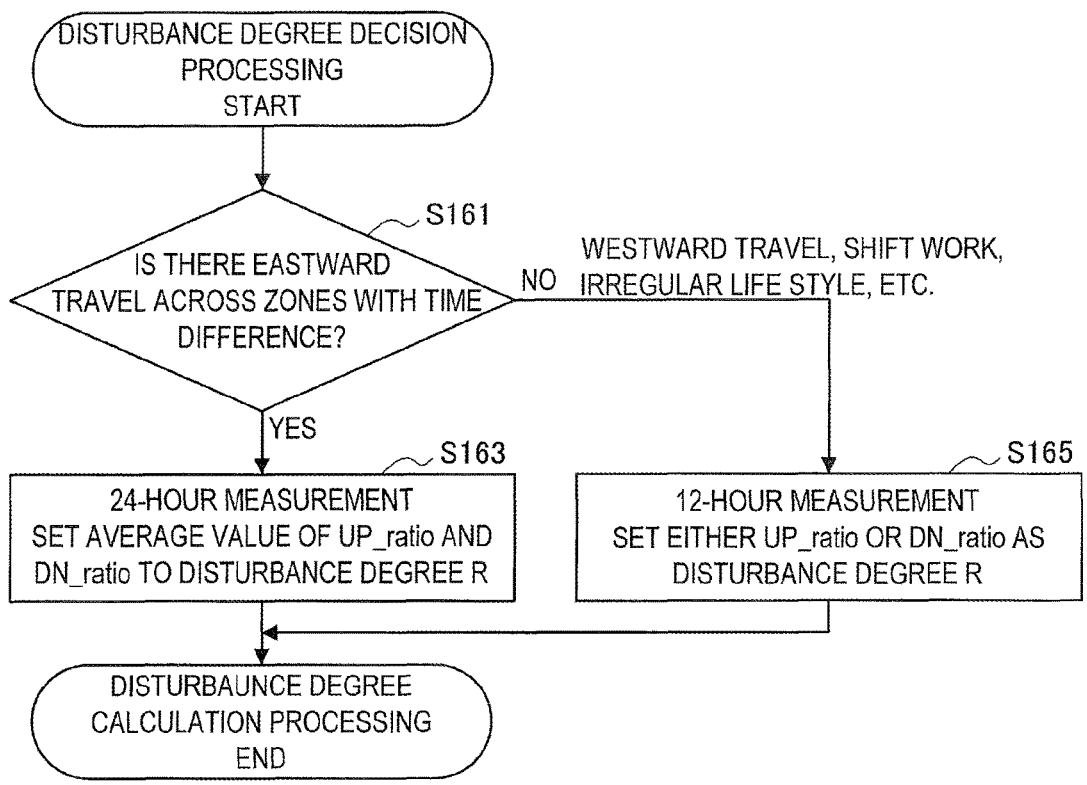
FIG. 17 is a flowchart illustrating a flow of disturbance degree decision processing.

Next, an example of the disturbance degree calculation processing according to the present embodiment is described with reference to FIGS. 13 to 17. FIG. 15 is a flowchart illustrating the overall flow of the disturbance degree calculation processing. FIG. 16 is a flowchart illustrating a flow of the shift amount extracting processing. FIG. 17 is a flowchart illustrating a flow of the disturbance degree decision processing.

With reference to FIG. 15, the physiological index derivation processing is performed first (S141). As for the physiological index derivation processing of Step S141, the processing is performed according to the kind of the acquired biomedical signal as described in connection with the reference information calculation processing (refer to FIGS. 13 and 14). Subsequently, the shift amount calculating unit 115 performs the shift amount calculation processing (S143). Here, a detailed example of the shift amount calculation processing of Step S143 is described with reference to FIG. 16.

The shift amount calculating unit 115 acquires the physiological index time series data S first (S151). Subsequently, the shift amount calculating unit 115 refers to information on the cause of the shift acquired by the prior information acquiring unit 113, and determines whether a subject has traveled across zones with a time difference (S153). Subsequently, when the subject has traveled across zones with a time different, the shift amount is calculated using a time in a travel destination (S155). Meanwhile, when the subject has not traveled across zones with a time difference, the shift amount is calculated using a current position (S157).

Referring again to FIG. 15 and continuing a description, subsequently, the disturbance degree deciding unit 117 executes the disturbance degree decision processing on a biological rhythm (S145). Hereinafter, a detailed example of the disturbance degree decision processing of Step S145 is described with reference to FIG. 17. The disturbance degree deciding unit 117 determines first whether an eastward travel across zones with a time difference is made or not based on prior information acquired by the prior information acquiring unit 113 (S161). Here, when it is determined that the eastward travel across zones with a time difference is made, the disturbance degree deciding unit 117 obtains the average value of the first shift amount UP_ratio and the second shift amount DN_ratio through a 24-hour measurement as the disturbance degree R (S163). Meanwhile, for a westward travel across zones with a time difference, shift work, irregular life style, etc., the disturbance degree deciding unit 117 can decide either the UP_ratio or the DN_ratio as the disturbance degree R through a 12-hour measurement (S165). Further, as described above, although the 24-hour measurement is performed only for the eastward travel across zones with a time difference, the present technology is not limited to this example. The 24-hour measurement may be performed regardless of the cause of the shift. Further, the 12-hour measurement may be performed regardless of the cause of the shift. In this case, for the eastward travel across zones with a time difference, the degree of shift is recovered, fluctuating up and down as described above.

Referring again to FIG. 15, after the disturbance degree R is decided, the output unit 119 outputs the calculated disturbance degree R (S147). Here, the output of the disturbance degree R may be performed using the display screen as described above, or performed by outputting voice.

(2-4. Examples of Effects)

Hereinabove, the disturbance degree calculating device 10 according to the first embodiment of the present disclosure has been described. According to the present embodiment, the disturbance degree of a biological rhythm can be quantitatively evaluated. In this case, during the period TP between the first reference time point $t_B$ and the second reference time point $t_E$, the disturbance degree is decided based on a ratio between a first area where the value of the physiological index time series data S is larger than the average value M and a second area where the value of the physiological index time series data S is smaller than the average value M, within the area of a region surrounded by a waveform of the time series data of the physiological index (for example, core temperature) derived from the biomedical signal, and a straight line indicating the average value of the physiological index time series data in daily life. By setting the first reference time point $t_B$ and the second reference time point $t_E$ to time points at which the physiological index in daily life is assumed to become the average value M, the shift amount in normal life can be set to 1, and the shift amount can be decreased as the disturbance degree of the biological rhythm is increased. In this manner, the value of the shift amount or the average value of the shift amount can be used as the value of the disturbance degree R as it is. When the first reference time point $t_B$ and the second reference time point $t_E$ are not set to the time points at which the physiological index in daily life is assumed to become the average value M, a difference between the shift amount in daily life and the shift amount during the inspection may be used as the disturbance degree R.

Further, by setting the first reference time point $t_B$ to a time point 6 hours before the peak time point of the physiological index time series data $S_b$, and a second reference time point $t_E$ to a time point 6 hours after the peak time point, the reference time point can be obtained with a small amount of calculation. When a subject does travel eastward across zones with a time difference, the disturbance degree of the biological rhythm can be more precisely expressed by setting the average value of the first shift amount UP_ratio and the second shift amount DN_ratio as the disturbance degree R.

<3. Second Embodiment (Example in which a Recovery Degree Prediction Function is Provided)>

(3-1. Configuration)

Figure 18:
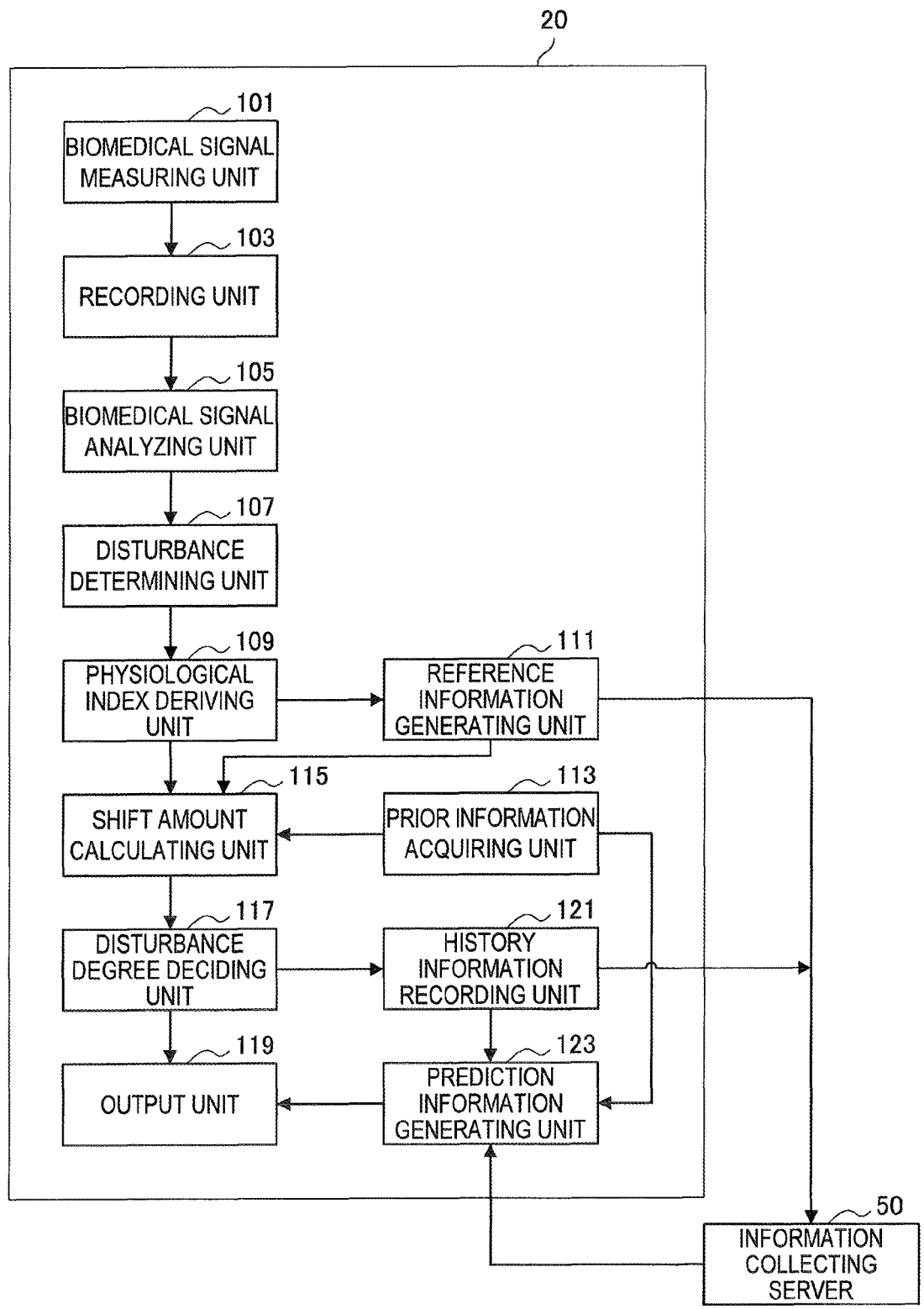
FIG. 18 is a block diagram illustrating a configuration of a biological rhythm disturbance degree calculating device according to a second embodiment of the present disclosure.
Figure 19:
FIG. 19 is an explanatory view illustrating an example of history information.
Figure 20:
FIG. 20 is an explanatory view illustrating an example of history information stored by an information collecting server.

Next, a configuration of a disturbance degree calculating device 20 according to a second embodiment of the present disclosure is described with reference to FIGS. 18 to 22. FIG. 18 is a block diagram illustrating the configuration of the biological rhythm disturbance degree calculating device according to the second embodiment of the present disclosure. FIG. 19 is an explanatory view illustrating an example of history information. FIG. 20 is an explanatory view illustrating an example of the history information stored by an information collecting server. FIG. 21 is an explanatory view illustrating an example of reference information stored by the information collecting server. FIG. 22 is an explanatory view illustrating another example of the reference information stored by the information collecting server.

First, referring to FIG. 18, the disturbance degree calculating device 20 mainly includes a biomedical signal measuring unit 101, a recording unit 103, a biomedical signal analyzing unit 105, a disturbance determining unit 107, a physiological index deriving unit 109, a reference information generating unit 111, a prior information acquiring unit 113, a shift amount calculating unit 115, a biological rhythm disturbance degree deciding unit 117, an output unit 119, a history information recording unit 121, and a prediction information generating unit 123.

That is, in addition to the configuration of the disturbance degree calculating device 10 according to the first embodiment of the present disclosure, the disturbance degree calculating device 20 further includes the history information recording unit 121 and the prediction information generating unit 123. Further, the disturbance degree calculating device 20 differs from the disturbance degree calculating device 10 in the point that it has a configuration which records reference information and history information of a disturbance degree R in an information collecting server 50. Further, a description about the same components as the disturbance degree calculating device 10 according to the first embodiment is omitted, and mainly a description about a difference with the disturbance degree calculating device 10 is made.

The history information recording unit 121 has a function which records the history information of the disturbance degree R of a subject. The history information recording unit 121 can record history information 22 of the disturbance degree R in a storage unit (now shown) in the disturbance degree calculating device 20, for example. For example, the history information 22 may include a cause of the disturbance, a shift time, a lapsed time (since the cause of the disturbance appears), and the disturbance degree R. Further, the history information recording unit 121 may add a user ID for identifying a subject to the history information 22, and may record it in the information collecting server 50 which can communicate via a network (history information 52).

Further, the information collecting server 50 can collect the history information 52 of the disturbance degrees R of multiple subjects and the reference information 54.

The prediction information generating unit 123 has a function which extracts history information based on a shift time of an activity time zone and the cause of the shift of the activity time zone which are acquired by the prior information acquiring unit 113, and a function which predicts the disturbance degree R based on the history information extracted. For this case, the prediction information generating unit 123 may extract history information from the history information 22 stored in the storage unit in the disturbance degree calculating device 20. Further, the prediction information generating unit 123 may extract history information from the history information 52 stored in the information collecting server 50. For this case, when the history information of a subject is not stored, the prediction information generating unit 123 can use the history information of a different subject. When the history information of a different subject is used, preferably, the prediction information generating unit 123 may use the history information on a different subject who has a similar biological rhythm in daily life to a target subject. For this case, the prediction information generating unit 123 can use the history information on a different subject who is similar in the reference information to the target subject. For example, when there is the physiological index time series data of the subject only for a period up to one day before, the prediction information generating unit 123 may generate the prediction information on the disturbance degree R corresponding to a period from two days before. For this case, the output unit 119 uses the value supplied from the disturbance degree deciding unit 117 as the disturbance degree R of a first day, and can output information on the disturbance degree R by adding the prediction information for a period starting from a second day.

For example, the reference information 54 stored in the information collecting server 50 may include a reference time point as illustrated in FIG. 21. In this case, reference information 54a can include a user ID, an average value M, a first reference time point $t_B$, and a second reference time point $t_E$. Further, the reference information 54 stored in the information collecting server 50 may include a shift amount when the reference time point is fixed as illustrated in FIG. 22. For this case, reference information 54b can include a user ID, an average value M, a first shift amount UP_ratio, a second shift amount DN_ratio, and information on a positive/negative sign of the physiological index at a time point $t_B$. Further, the information on the positive/negative sign may be information on the positive/negative sign of the physiological index at a time point $t_E$.

(3-2. Prediction Information Generation Processing)

Figure 23:
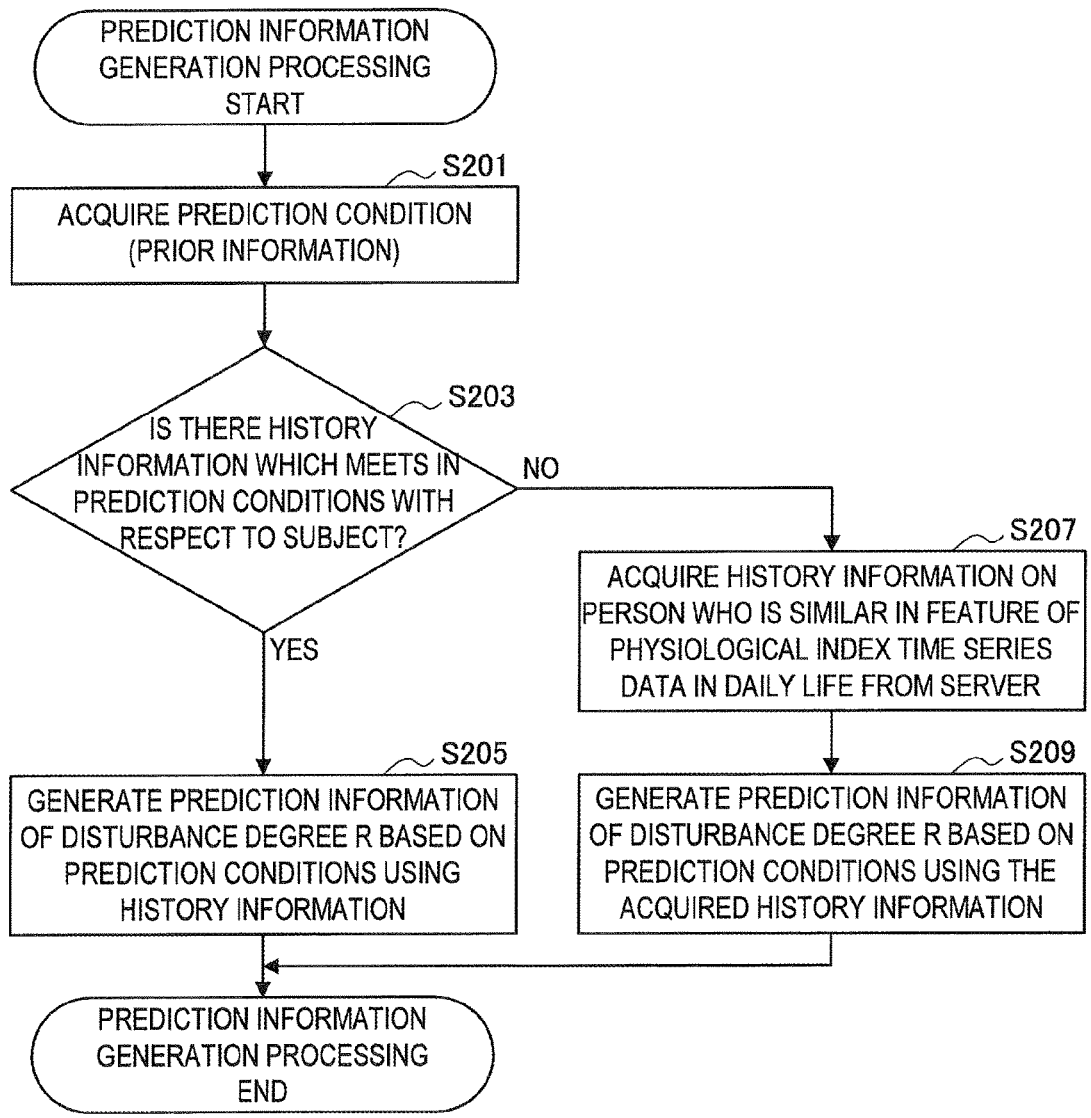
FIG. 23 is a flowchart illustrating a flow of predication information generation processing.
Figure 24:
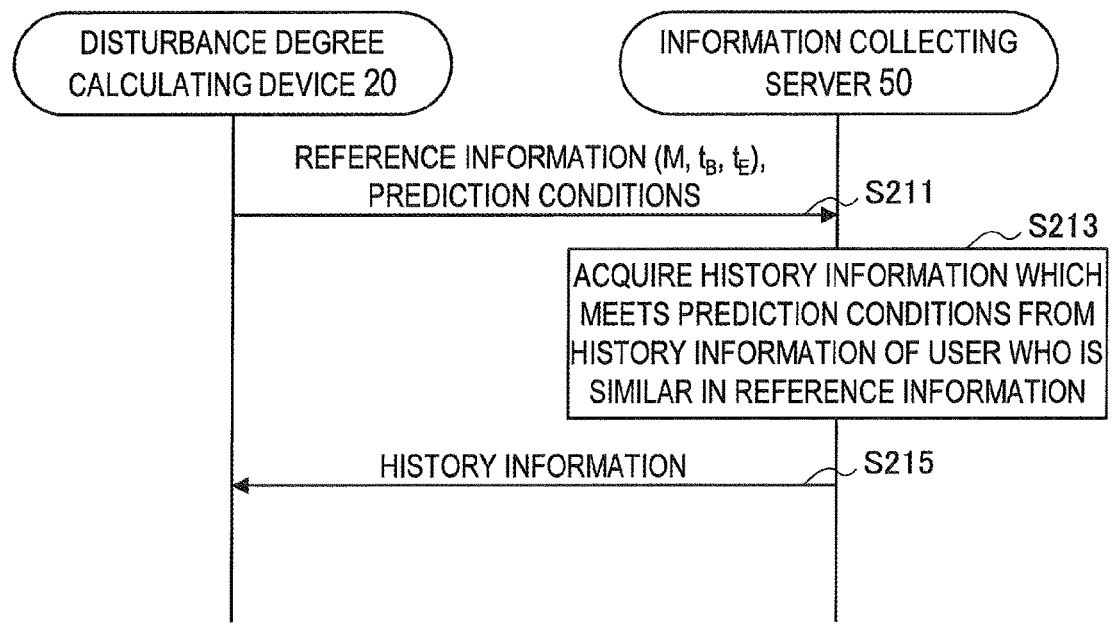
FIG. 24 is a sequence diagram showing a flow of acquisition of the history information from the information collecting server.

Next, prediction information generation processing among operations of the disturbance degree calculating device 20 is described with reference to FIGS. 23 and 24. FIG. 23 is a flowchart illustrating a flow of the prediction information generation processing. FIG. 24 is a sequence diagram illustrating a flow of a process of acquiring the history information from the information collecting server.

The prediction information generating unit 123 first acquires prior information acquired by the prior information acquiring unit 113 as prediction conditions (S201). Subsequently, the prediction information generating unit 123 determines whether there is history information which meets the prediction conditions with respect to the subject himself/herself, based on the acquired prediction conditions (S203). When there is the history information which meets the prediction conditions with respect to the subject himself/herself, the prediction information on the disturbance degree R is generated based on the prediction conditions using the history information of the subject himself/herself (S205). On the other hand, in Step S203, when there is no history information which meets the prediction conditions with respect to the subject himself/herself, the prediction information generating unit 123 acquires the history information of a different subject who is similar in features of the physiological index time series data S in normal life to the subject, from the server (S207).

The details of the processing in Step S207 are described with reference to FIG. 24. The disturbance degree calculating device 20 transmits reference information (M, $t_B$, $t_E$) and the prediction conditions acquired by the prior information acquiring unit 113 to the information collecting server 50 (S211). The information collecting server 50 extracts the user ID of a subject which is most similar in the reference information to the subject from among items of the reference information 54a stored, based on the reference information received. Subsequently, the information collecting server 50 acquires the history information which meets the prediction conditions from among items of the history information 52 of the subject having the user ID which is extracted (S213). Subsequently, the information collecting server 50 transmits the acquired history information to the disturbance degree calculating device 20 (S215). Further, although the example in which the reference time point is included in the reference information has been described, the present technology is not limited the example. For example, the reference information may also include the shift amount. When the reference information includes the shift amount, the prediction information generating unit 123 transmits the shift amount and the average value M to the information collecting server 50, along with the positive/negative information of the physiological index at the time point $t_B$. The information collecting server 50 can extract the history information of a certain subject who is similar in the shift amount and the average value M to the subject and is identical in the negative/positive information of the physiological index at the time point $t_B$ to the subject.

The prediction information generating unit 123 which has acquired the history information from the information collecting server 50 in this manner generates the prediction information on the disturbance degree R based on the prediction conditions using the acquired history information. For example, when there is one item of the acquired history information, the disturbance degree R in the acquired history information may be used as the prediction information as it is. Further, when there are multiple items of the acquired history information, the average value of the disturbance degrees R in the acquired history information may be used as the prediction information.

(3-3. Examples of Effects)

According to the disturbance degree calculating device 20 according to the second embodiment of the present disclosure described above, not only a disturbance degree R of the biological rhythm at present but also a disturbance degree R for future can be predicted. The level of recovery of the biological rhythm varies depending on individuals. For this reason, when there is the history information of the subject himself/herself, use of the history information of the subject himself/herself increases a possibility that the accuracy of prediction increases. However, it cannot be said that the history information of the subject himself/herself necessarily exists. For this reason, the disturbance degree calculating device 20 has a configuration which enables use of the history information of a different subject. For this case, the disturbance degree calculating device 20 can use the history information of a subject who is similar in the feature of the biological rhythm in daily life to a target subject among other subjects. As described above, the level of recovery of the biological rhythm varies depending on individuals. Usually, the subjects who are similar in the feature of the biological rhythm in daily life to each other are considered to be also similar in the level of recovery when the biological rhythm is disturbed. For this reason, the accuracy of prediction can be comparatively increased by using the history information of the subject who is similar in the reference information in daily life to the target subject among other subjects.

<4. Third Embodiment (Example of Service using Data of Multiple users which is Collected)>

Next, a third embodiment of the present disclosure is described. The present embodiment is an example of service using reference information which can be acquired by the disturbance degree calculating device 10 or the disturbance degree calculating device 20 described above.

(4-1. Configuration)

Figure 25:
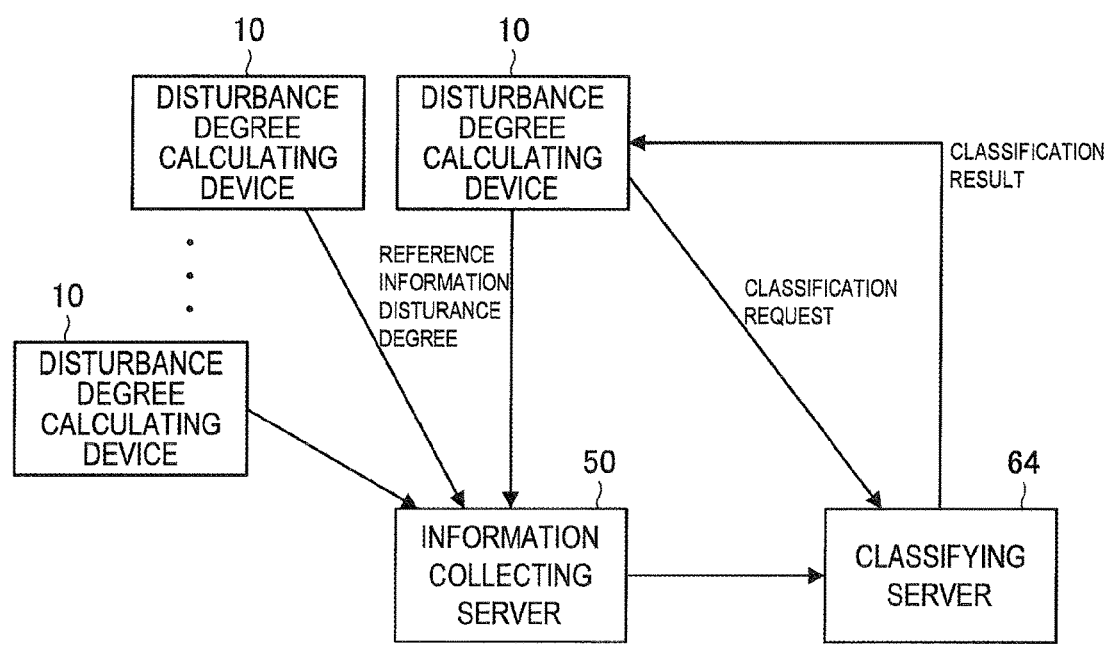
FIG. 25 is an explanatory view illustrating a configuration of a system which uses a disturbance degree of a biological rhythm according to a third embodiment of the present disclosure.

Here, the service provided by the present embodiment is described with reference to FIG. 25. FIG. 25 is an explanatory view illustrating a configuration of a system which uses the disturbance degree of the biological rhythm according to the third embodiment of the present disclosure. First, the service described here is provided by a service server 60. A service server 60 is an example of a classifying device having a function which classifies users into a morning type, a night type, or an ordinary type in response to a classification request from a user's terminal device (here, the disturbance degree calculating device 10). For this case, reference information 54 collected by an information collecting server 50 is used by the service server 60. The service server 60 can transmit a classification result to the user's terminal device which is a transmission source of the classification request.

(4-2. Morning Type/Night Type Classification Processing)

Figure 26:
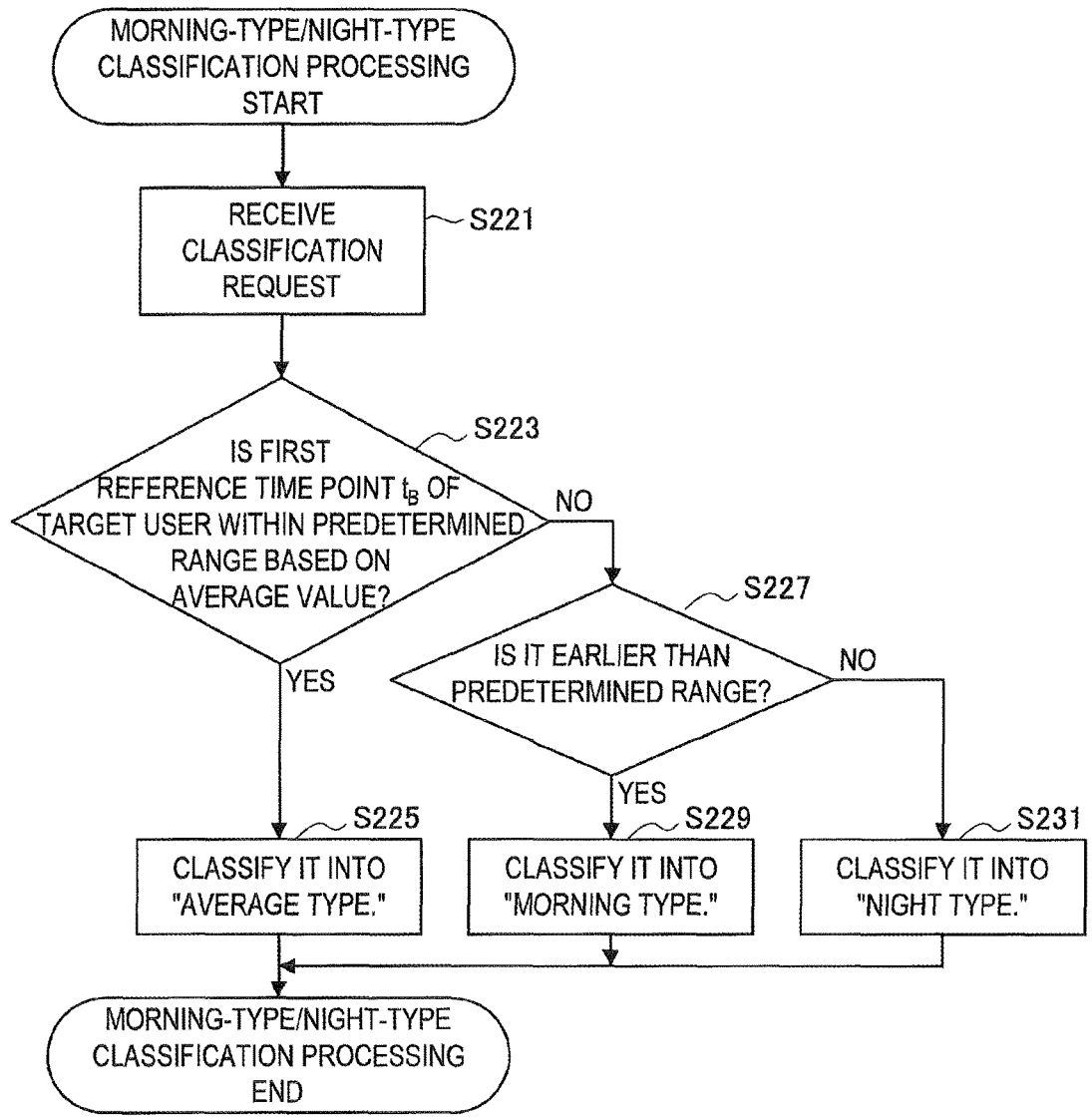
FIG. 26 is a flowchart illustrating a flow of morning-type/night-type classification processing.

Next, morning type/night type classification processing is described with reference to FIG. 26. FIG. 26 is a flowchart illustrating a flow of the morning type/night type classification processing. The service server 60 receives a classification request from the disturbance degree calculating device 20 first (S221). Subsequently, the service server 60 determines whether a first reference time point $t_B$ of a target user is within a predetermined range compared to the average value of the first reference time point $t_B$ with respect to multiple subjects (S223).

In Step S223, when it is determined that the first reference time point $t_B$ is within the predetermined range, the service server 60 classifies this user into an "averaged type" (S225). On the other hand, in Step S223, when it is determined that the first reference time point $t_B$ is not within the predetermined range, the service server 60 determines whether the first reference time point $t_B$ is shifted to be earlier in time than the predetermined range (S227). When it is determined that the first reference time point $t_B$ is shifted to be rubbed against the predetermined range in Step S227, the service server 60 classifies this user into the "morning type" (S229). On the other hand, when it is determined that the first reference time point $t_B$ is shifted to be later than the predetermined range in Step S227, the service server 60 classifies this user into the "night type" (S231).

(4-3. Examples of Effects)

According to the third embodiment of the present disclosure described above, a user can be classified into a morning type, a night type, or an ordinary type using the reference information acquired by the disturbance degree calculating device 10. There is an individual difference in a biological rhythm. For this reason, among users, it is considered that there is a potential demand that the users want to be aware of their types of the biological rhythm, for example, the morning type, the night type, or the average type. According to the present embodiment, users can be provided with useful classification information based on the average value of a plurality of subjects.

<5. Fourth Embodiment>

Figure 27:
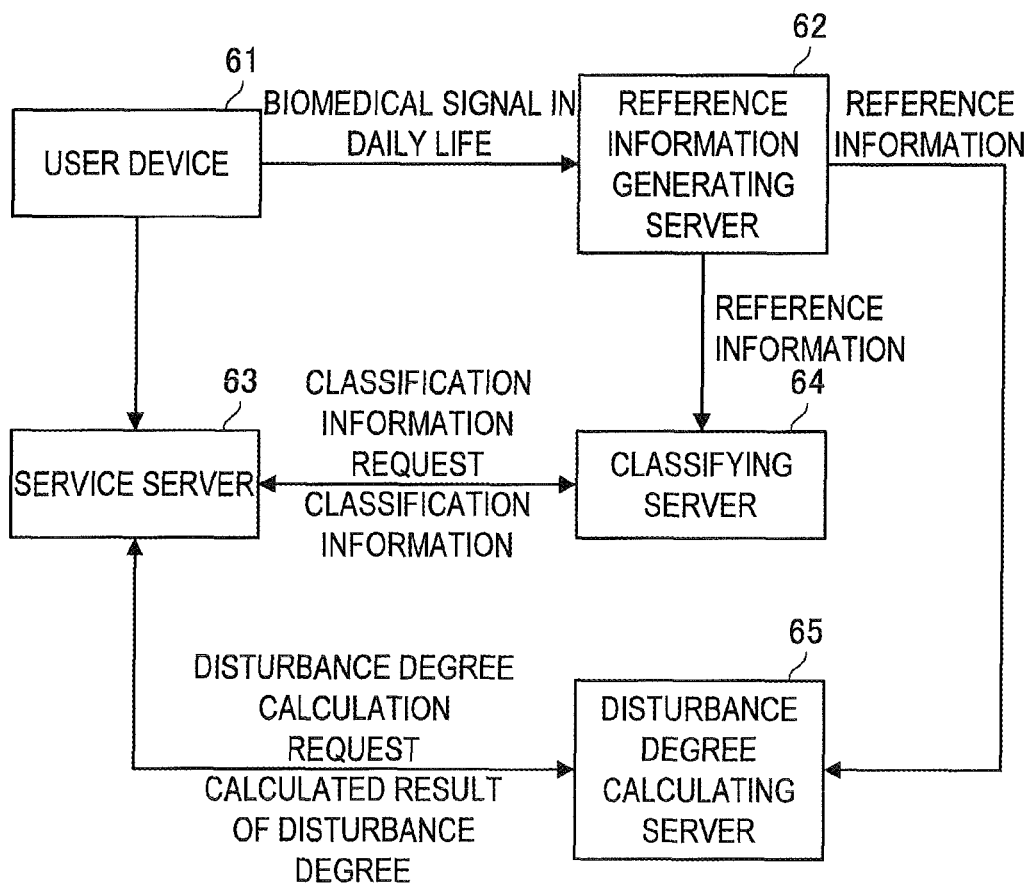
FIG. 27 is an explanatory view illustrating a configuration of a system which uses a disturbance degree of a biological rhythm according to a fourth embodiment of the present disclosure.

Next, a configuration of a disturbance degree calculating system according to a fourth embodiment of the present disclosure is described with reference to FIG. 27. For example, the disturbance degree calculating system includes a user device 61, a reference information generating server 62, a service server 63, a classifying server 64, and a disturbance degree calculating server 65.

The user device 61 is an information processing apparatus having a function which acquires a biomedical signal. The user device 61 may be an information processing apparatus, such as a mobile phone, a portable music reproducing device, a portable video processing device, or a portable game machine, for example. The user device 61 may be set such as to acquire the biomedical signal in daily life and transmit the acquired biomedical signal to the reference information generating server 62. The transmission of the biomedical signal may be set such as to be performed periodically or continuously. Alternatively, setting may be made such that the biomedical signal is transmitted periodically or continuously for a certain period of time so that the reference information can be generated, and the generated reference information is used. Further, the user device 61 can transmit various kinds of information required for use of service to the service server 63, when using the service provided by the service server 63.

The reference information generating server 62 has a function which generates reference information from the biomedical signal received from the user device 61. The reference information generating server 62 can receive the biomedical signals from a plurality of user devices 61 and can generate the reference information on each user. In this case, the reference information generating server 62 can cause the generated reference information to be stored along with signs used to identify each user (subject). The reference information generating server 62 can provide the reference information of a specific user in response to the request from the classifying server 64 or the disturbance degree calculating unit 65.

Figure 28:
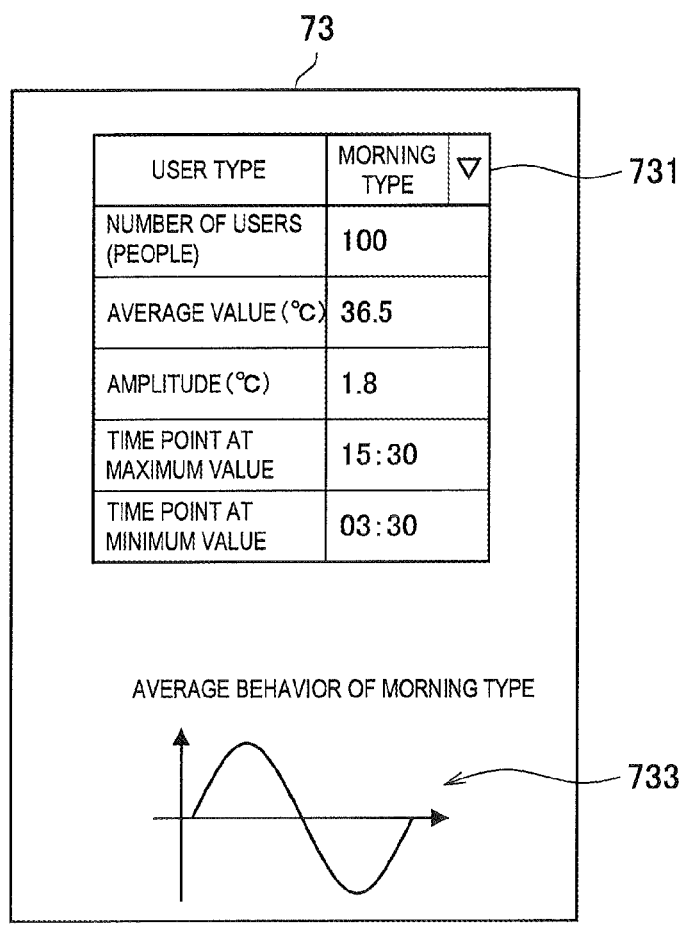
FIG. 28 is an explanatory view illustrating an example of a screen which displays classification information provided in the embodiment.
Figure 29:
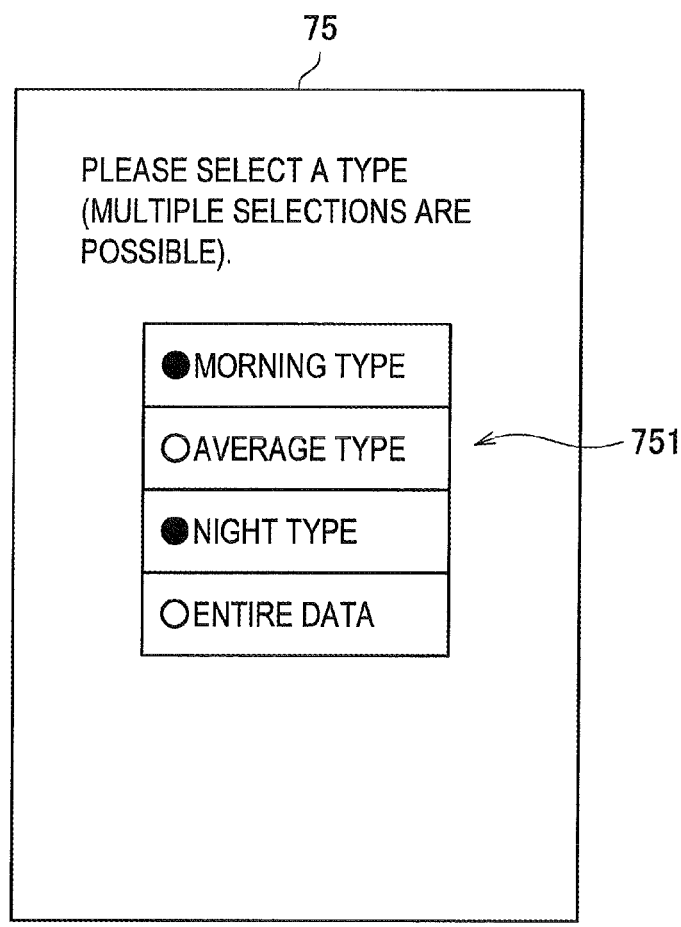
FIG. 29 is an explanatory view illustrating another example of the screen which displays the classification information provided in the embodiment.
Figure 30:
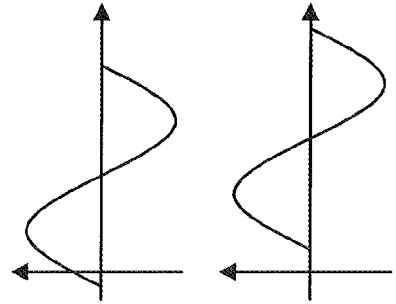
FIG. 30 is an explanatory view illustrating another example of the screen which displays the classification information provided in the embodiment.
Figure 31:
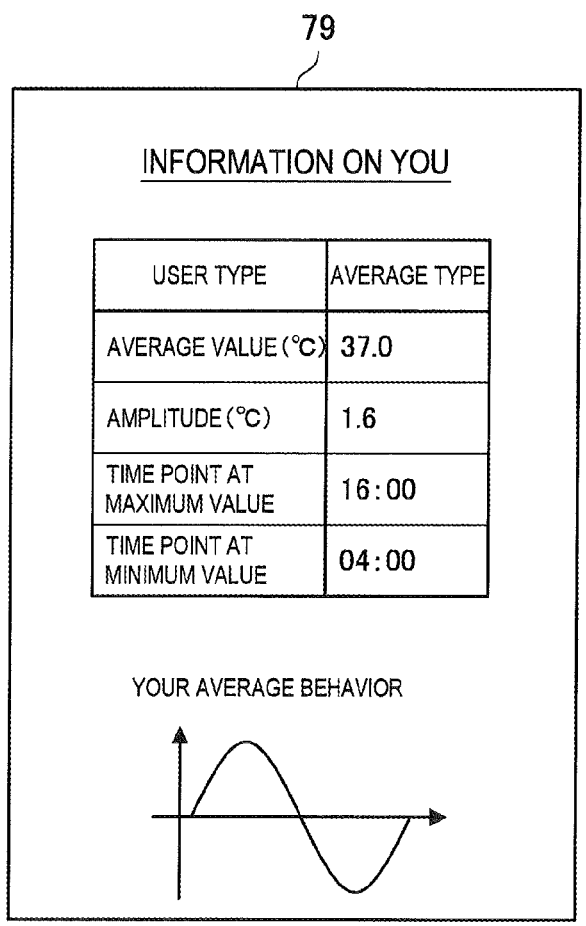
FIG. 31 is an explanatory view illustrating another example of the screen which displays the classification information provided in the embodiment.

The service server 63 has a function which provides the user device 61 with various kinds of information. The service server 64 provides the user device 61 with a display screen illustrated in FIGS. 28 to 34 and described below, and can change a display content by causing the classifying server 64, the disturbance degree calculating unit 65, etc. to generate the information to be contained in the display screen in response to user's operation with respect to the display screen. For example, the service server 64 can transmit information on a specific user type specified by the user device 61 to the classifying server 64 and acquire classification information including the average value of the reference information or the like on a plurality of users belonging to the user type specified. If a user selects a user type (classification) within an input area 731 in the display screen 73 as illustrated in FIG. 28 the service server 63 may provide the user device 61 with the display screen 73 including the classification information on the selected user type. Alternatively, as illustrated in FIG. 29, the classification information on the user type(s) (multiple selections are possible) which the user has selected within the display screen 75 which is provided for user's selection of user type may be acquired from the classifying server 64, and the display screen 77 (FIG. 30) including the acquired classification information may be generated and provide to the user device 61.

Alternatively, the service server 63 can acquire the classification information on the user by transmitting the user's identifier to the classifying server 64. At this time, the classifying server 64 can acquire the reference information on the user from the reference information generating server 62 based on the user's identifier, and can classify the user into any type based on the reference information. The service server 63 can provide the user device 61 with the classification information on a specific user, acquired from the classifying server 64, in the form of the display screen 79 illustrated in FIG. 31. Although the service server 63 is configured to cause the classifying server 64 to acquire the reference information from the reference information generating server 62 by transmitting the user's identifier, the present technology is not limited to that example. For example, when the user device 61 holds user's own reference information, the service server 63 may acquire the reference information from the user device 61 and may transmit it to the classifying server 64. At this time, the classifying server 64 can classify the user type of the user using the reference information acquired from the service server 63.

Figure 32:
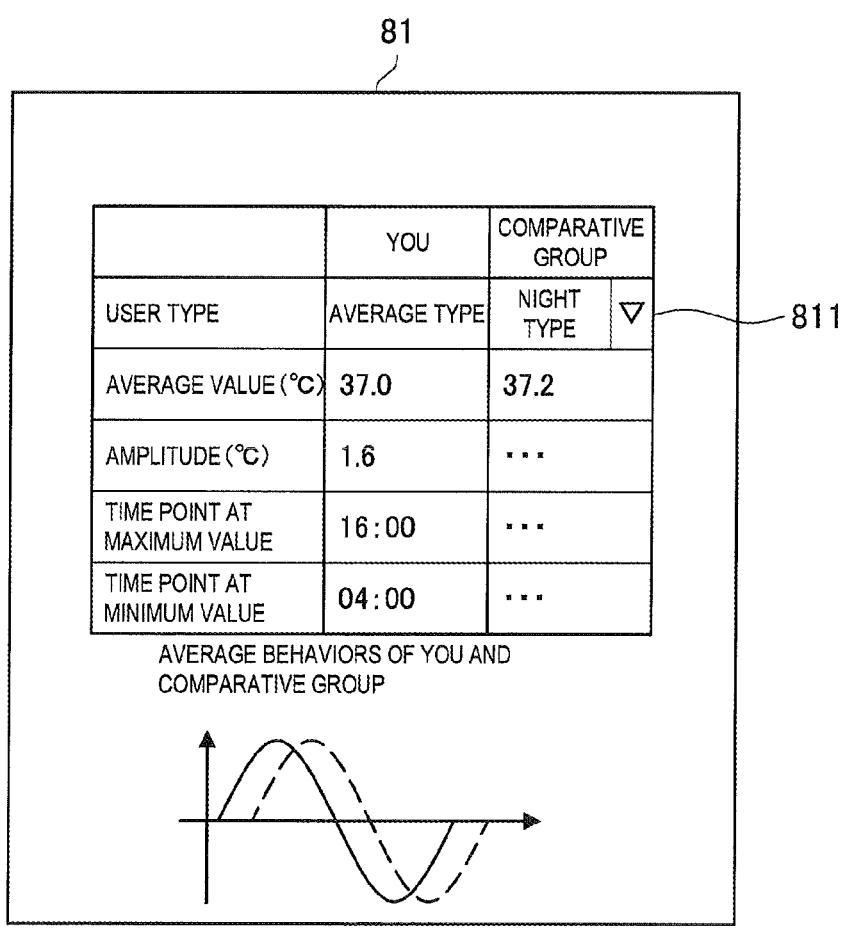
FIG. 32 is an explanatory view illustrating another example of the screen which displays the classification information provided in the embodiment.

Further, the service server 63 can also generate the display screen 81 illustrated in FIG. 32 by combining the above-described functions. That is, the service server 63 may acquire the classification information of the user from the information which identifies a specific user and then generate the display screen 81 according to the classification information on the user type of the specific user. According to the display screen 81, the user can compare own information with the information on other people of the other user types. The user can refer to the reference information on people of a selected user type by selecting a user type, with which the user wants to compare, in the input area 811 of the display screen 81.

Further, the service server 63 can transmit information including at least the prior information which is acquired from the user device 61 to the disturbance degree calculating server 65, and can acquire a calculated result of the disturbance degree. For this case, the service server 63 may acquire the biomedical signal at the time of an inspection from the user device 61, and may transmit it to the disturbance degree calculating device 65. The disturbance degree calculating device 65 may actually calculate the disturbance degree of the user from the prior information and the biomedical signal which were acquired. Alternatively, the disturbance degree calculating device 65 can also predict user's disturbance degree based on the prior information.

Figure 33:
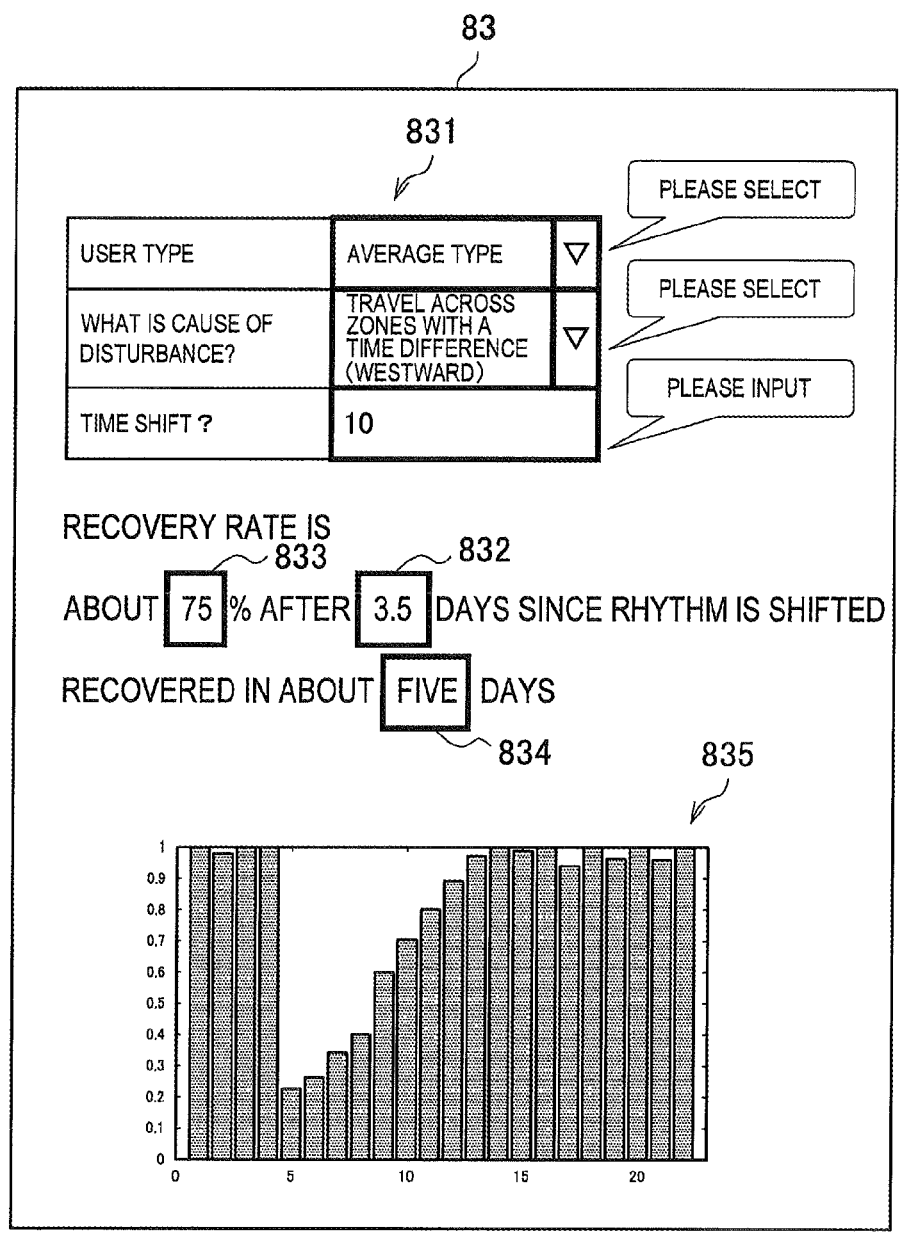
FIG. 33 is an explanatory view illustrating an example of a screen which displays information on a disturbance degree provided in the embodiment.

The service server 63 can provide the user device 61 with the display screen 83 as illustrated, for example, in FIG. 33. At this time, the service server 63 can display the prediction result of the disturbance degree of the user by transmitting the prior information, which is input or selected by the user via the selected area 831, to the disturbance degree calculating unit 65. For example, a user may be provided with the prediction result of the disturbance degree in the form of a graph 835. Further, the service server 63 may display to which extent the disturbance is recovered after how many days and how many hours it will take until the recovery rate becomes about 100%. The conditions of the data displayed at this time may be decided beforehand. Alternatively, the service server 63 may display the time which will be taken until the recovery rate becomes about 100% in a region 834, and may display the recovery rate by calculating the recovery rate to be displayed in the region 833 according to the conditions input to the region 832. Alternatively, the service server 63 may calculate the number of days to be displayed on the region 832 according to the conditions which are input to the region 833, and may display it. According to the display screen 83, the user can be aware of the disturbance degree of the biological rhythm of a person of the user type which is selected by the user, by allowing the user to select the situation leading to the disturbance.

Alternatively, the service server 63 may provide the user device 61 with a display screen 85 as illustrated in FIG. 34. The display screen 85 can display the disturbance degree of a specific user. At this time, the service server 63 acquires the information for identifying a user from the user device 61, and transmits it to the classifying server 64. Next, the service server 63 can generate the display screen 85 including information on the user type of the specific user acquired from the classifying server 64. According to the display screen 85, the user selects the situation leading to the disturbance of the user himself/herself, and can be aware of the disturbance degree at that time.

The preferred embodiments of the present disclosure have been described above with reference to the accompanying drawings, whilst the present disclosure is not limited to the above examples, of course. A person skilled in the art may find various alternations and modifications within the scope of the appended claims, and it should be understood that they will naturally come under the technical scope of the present disclosure.

For example, although it is assumed that the information collecting server 50 and the disturbance degree calculating devices 10 and 20 are separate devices in the first, second, and third embodiments, the present technology is not limited to the embodiments. For example, the information collecting server 50 and the disturbance degree calculating devices 10 and 20 may be realized as an integrated device, and perform disturbance degree calculation processing by receiving a biomedical signal from user's terminal device.

Each embodiment shown here illustrates an example and each function described as a function of the disturbance degree calculating device can be realized by a plurality of devices. Each function of the disturbance degree calculating device 10 or the disturbance degree calculating device 20 may be realized by a plurality of devices. For example, the sensor which acquires subject's biomedical signal, the device which calculates the disturbance degree R, and the device which outputs the calculated result of the disturbance degree R may be separate devices, respectively. Further, a terminal device having functions of the biomedical signal measuring unit 101, the recording unit 103, and the output unit 119 may transmit a biomedical signal acquired, via a wireless communication channel, to a server, which is a different body, having functions of the biomedical signal analyzing unit 105, the disturbance determining unit 107, the physiological index deriving unit 109, the reference information generating unit 111, the prior information acquiring unit 113, the shift amount calculating unit 115, and the disturbance degree deciding unit 117. At this time, the server transmits an analysis result to the terminal device. The terminal device may be a portable type, wristwatch type, or stationary type. The sensor which acquires the biomedical signal may be built in the terminal device, or may be provided as a separate device. When the terminal device and the sensor are provided as separate bodies, the sensor transmits the biomedical signal acquired to the terminal device via a wired or wireless communication channel. Further, not only the form in which each function of the server is realized by one server but also the form in which the above-described functions are realized by distributed processing using a plurality of servers may fall within the scope of the present technology.

Furthermore, the steps described in the flowchart in the present specification include processes which are serially performed according to the described order, but are not necessarily serially performed. The steps include not only processes which are serially performed but also processes performed in parallel or individually. Even for the steps serially processed, it is needless to say that the order of the steps may be suitably changed depending on the cases.

Additionally, the present technology may also be configured as below.

(1)

A biological rhythm disturbance degree calculating device, including:

a physiological index time series data acquiring unit which acquires time series data of a physiological index calculated from a biomedical signal of a subject;

a calculation period deciding unit which decides a calculation period which is a time length corresponding to substantially a half of a cycle with which daily-life physiological index time series data calculated from the biomedical signal measured in daily life fluctuates;

a calculating unit which calculates, during the calculation period, a phase shift amount between inspected physiological index time series data calculated from the biomedical signal measured during an inspection and the daily-life physiological index time series data; and a disturbance degree deciding unit which decides a disturbance degree of a biological rhythm during the inspection of the subject based on the phase shift amount.

(2)

The biological rhythm disturbance degree calculating device according to (1), wherein the calculating unit calculates the shift amount based on a ratio between a first feature quantity corresponding to the inspected physiological index time series data which has a value larger than an average value of the daily-life physiological index time series data, and a second feature quantity corresponding to the inspected physiological index time series data which has a value smaller than the average value.

(3)

The biological rhythm disturbance degree calculating device according to (2), wherein the first feature quantity is an area of a region surrounded by a waveform of the inspected physiological index time series data which has a larger value than the average value and by a straight line indicating the average value, and wherein the second feature quantity is an area of a region surrounded by a waveform of the inspected physiological index time series data which has a smaller value than the average value and by the straight line indicating the average value.

(4)

The biological rhythm disturbance degree calculating device according to (2), wherein the first feature quantity is a time length of a period during which the inspected physiological index time series data has a larger value than the average value, and wherein the second feature quantity is a time length of a period during which the inspected physiological index time series data has a smaller value than the average value.

(5)

The biological rhythm disturbance degree calculating device according to any one of (1) to (3), wherein the calculation period deciding unit sets the calculation period to a period between a first reference time point at which a value of the daily-life physiological index time series data changes from the average value or less to the average value or more, and a second reference time point at which the value of the daily-life physiological index time series data changes from the average value or more to the average value or less.

(6)

The biological rhythm disturbance degree calculating device according to (5), wherein the calculating unit sets a ratio of the first feature quantity as the phase shift amount during a first calculation period ranging from the first reference time point to the second reference time point, and further sets a ratio of the second feature quantity as the phase shift amount during a second calculation period ranging from the second reference time point to the first reference time point.

(7)

The biological rhythm disturbance degree calculating device according to (6), wherein the disturbance degree deciding unit sets any one of the phase shift amount during the first calculation period, the phase shift amount during the second calculation period, and an average value of the phase shift amount during the first calculation period and the phase shift amount during the second calculation period, as the disturbance degree.

(8)

The biological rhythm disturbance degree calculating device according to (7), further including:

an activity time zone information acquiring unit which acquires a time shift of an activity time zone of the subject which leads to the disturbance of the biological rhythm, and a cause of a shift of the activity time zone, wherein the disturbance degree deciding unit sets an average value of the phase shift amount during the first calculation period and the phase shift amount during the second calculation period as the disturbance degree when the cause of the shift of the activity time zone is an eastward travel across zones with a time difference.

(9)

The biological rhythm disturbance degree calculating device according to (8), further including:

a history information acquiring unit which acquires history information of the disturbance degree; and a prediction information generating unit which predicts the disturbance degree based on the time shift and the history information extracted based on the cause of the shift.

(10)

The biological rhythm disturbance degree calculating device according to (9), wherein the history information acquiring unit acquires history information of another subject who is similar in reference information to the subject, when there are no pieces of history information which match in the time shift and the cause of the shift within the history information on the subject.

(11)

The biological rhythm disturbance degree calculating device according to any one of (8) and (9), wherein the activity time zone information acquiring unit detects that the cause of the shift of the activity time zone is a travel across zones with a time difference, based on a change in positional information of the subject, and further detects corresponding time difference.

(12)

The biological rhythm disturbance degree calculating device according to any one of (8) to (11), wherein the activity time zone information acquiring unit estimates the time shift of the activity time zone of the subject based on a detection value of a motion sensor which detects motion of the subject.

(13)

The biological rhythm disturbance degree calculating device according to any one of (5) to (12), wherein the biomedical signal is a signal having a biological rhythm of a circadian rhythm, and wherein the calculation period deciding unit sets the calculation period to a time period when the first reference time point is set to a time point 6 hours prior to a peak time point in the daily-life physiological index time series data and when the second reference time point is set to a time point 6 hours behind the peak time point.

(14)

The biological rhythm disturbance degree calculating device according to any one of (1) to (13), wherein the biomedical signal is a signal indicating a value of a core temperature.

(15)

The biological rhythm disturbance degree calculating device according to any one of (1) to (14), wherein the biomedical signal is a signal indicating a pulse wave and the physiological index is one of a pulse rate and an augmentation index (AI) value.

(16)

A classifying device including:

an information acquiring unit which acquires an average value of time series data of a physiological index calculated from a daily life biomedical signal with respect to a plurality of subjects, and a first reference time point and a second reference time point based on the average value; and a classifying unit which classifies a biological rhythm of a specific subject into any one type among a morning type, a night type, and an average type, based on information acquired by the information acquiring unit.

(17)

A biological rhythm disturbance degree calculating system including:

a user device including an estimation condition input unit, to which estimation conditions including a time shift of an activity time zone, and a cause of a shift of the activity time zone are input, and a transmitting unit which transmits the estimation conditions to a server; and the server including an acquiring unit which acquires a disturbance degree of a biological rhythm with respect to a plurality of subjects, the disturbance degree of the biological rhythm being calculated based on a phase shift amount between inspected physiological index time series data calculated from a biomedical signal measured during an inspection and daily life physiological index time series data, during a calculation period which is a time length corresponding to substantially a half of a cycle with which daily-life physiological index time series data calculated from the biomedical signal measured in daily life fluctuates, an estimating unit which estimates the disturbance degree under the estimation conditions using the disturbance degrees with respect to the plurality of subjects, and a display screen generating unit which generates a display screen including information on the estimated disturbance degree and which provides the user device with the display screen.

(18)

A biological rhythm disturbance degree calculating method, including:

acquiring physiological index time series data calculated from a biomedical signal of a subject;

deciding a calculation period having a time length which is substantially a half of a cycle with which daily-life physiological index time series data calculated from the biomedical signal measured in daily life fluctuates;

calculating, during the calculation period, a phase shift amount between inspected physiological index time series data calculated from the biomedical signal measured during an inspection and the daily-life physiological index time series data; and deciding a disturbance degree of a biological rhythm during the inspection of the subject based on the phase shift amount.

(19)

A program causing a computer to execute a biological rhythm calculating method including:

acquiring physiological index time series data calculated from a biomedical signal of a subject;

deciding a calculation period having a time length which is substantially a half of a cycle with which daily-life physiological index time series data calculated from the biomedical signal measured in daily life fluctuates;

calculating, during the calculation period, a phase shift amount between inspected physiological index time series data calculated from the biomedical signal measured during an inspection and the daily-life physiological index time series data; and deciding a disturbance degree of a biological rhythm during the inspection of the subject based on the phase shift amount.

(20)

A computer-readable recording medium storing a program which causes a computer to execute a biological rhythm disturbance degree calculating method including:

acquiring physiological index time series data calculated from a biomedical signal of a subject;

deciding a calculation period having a time length which is a half of a cycle with which daily-life physiological index time series data calculated from the biomedical signal measured in daily life fluctuates;

calculating, during the calculation period, a phase shift amount between inspected physiological index time series data calculated from the biomedical signal measured during an inspection and the daily-life physiological index time series data; and deciding a disturbance degree of a biological rhythm during the inspection of the subject based on the phase shift amount.

REFERENCE SIGNS LIST 10 disturbance degree calculating device
101 biomedical signal measuring unit
103 recording unit
105 biomedical signal analyzing unit
107 disturbance determining unit
109 physiological index deriving unit
111 reference information generating unit
113 prior information acquiring unit
115 feature quantity calculating unit
117 disturbance degree deciding unit
119 output unit
121 history information recording unit
123 prediction information generating unit

The invention claimed is:

1. A device, comprising:

a display screen; and a central processing unit (CPU) configured to:

acquire estimation conditions including:

a time shift of an activity time zone of a first subject of a plurality of subjects, and a cause of the time shift of the activity time zone, wherein the cause of the time shift is one of an eastward travel across first zones with a first time difference or a westward travel across second zones with a second time difference;

transmit the estimation conditions to a server;

acquire, from the server, first history information of the first subject of the plurality of subjects based on the estimation conditions;

acquire first physiological index time series data of a physiological index and second physiological index time series data of the physiological index, wherein the acquisition of the first physiological index time series data and the second physiological index time series data is based on a biomedical signal of the first subject acquired by a plurality of sensors, the first physiological index time series data of the first subject is based on the biomedical signal measured during a first time duration, and the second physiological index time series data of the first subject is based on the biomedical signal measured during a second time duration;

determine a first calculation period and a second calculation period based on the first physiological index time series data;

calculate, in the first calculation period, a first phase shift amount between the second physiological index time series data and the first physiological index time series data, where the first phase shift amount is calculated based on a first ratio between a first feature quantity, and a sum of the first feature quantity and a second feature quantity, wherein the first feature quantity corresponds to a first value of the second physiological index time series data, the first value of the second physiological index time series data is calculated using amplitudes of the second physiological index time series data that are larger than an average amplitude value of the first physiological index time series data, the second feature quantity corresponds to a second value of the second physiological index time series data, and the second value of the second physiological index time series data is calculated using amplitudes of the second physiological index time series data that are smaller than the average amplitude value of the first physiological index time series data;

calculate, in the second calculation period, a second phase shift amount between the second physiological index time series data and the first physiological index time series data, wherein the second phase shift amount is calculated based on a second ratio between the second feature quantity, and the sum of the first feature quantity and the second feature quantity;

set, based on the eastward travel and the first history information, an average value of the first phase shift amount and the second phase shift amount, as a disturbance degree of a biological rhythm of the first subject;

set, based on the westward travel and the first history information, one of the first phase shift amount or the second phase shift amount, as the disturbance degree of the biological rhythm;

generate information that indicates a recovery rate, the disturbance degree of the biological rhythm, and a recovery time of the first subject, wherein the recovery rate is based on the estimation conditions; and control the display screen to display the information that indicates the recovery rate, the disturbance degree, and the recovery time of the first subject.

2. The device according to claim 1, wherein
the first feature quantity is a first area of a first region surrounded by each of a first waveform of the second physiological index time series data and a straight line indicating the average amplitude value of the first physiological index time series data, and
the second feature quantity is a second area of a second region surrounded by each of a second waveform of the second physiological index time series data and the straight line.

3. The device according to claim 1, wherein
the first feature quantity is a first time length of a first time period, and
the second feature quantity is a second time length of a second time period.

4. The device according to claim 1, wherein
the CPU is further configured to set the first calculation period to a time period between a first reference time at which a value of the first physiological index time series data changes from a third value to a fourth value and a second reference time at which the value of the first physiological index time series data changes from a fifth value to a sixth value,
the third value is equal to or less than the average amplitude value of the first physiological index time series data,
the fourth value is greater than the average amplitude value of the first physiological index time series data,
the fifth value is equal to or greater than the average amplitude value of the first physiological index time series data, and
the sixth value is less than the average amplitude value of the first physiological index time series data.

5. The device according to claim 4, wherein
the first feature quantity and the second feature quantity for the first phase shift amount are obtained in the first calculation period that ranges from the first reference time to the second reference time, and
the first feature quantity and the second feature quantity for the second phase shift amount are obtained in the second calculation period that ranges from the second reference time to a third reference time.

6. The device according to claim 1, wherein the CPU is further configured to detect the time shift of the activity time zone based on a change in positional information of the first subject.

7. The device according to claim 1, wherein the CPU is further configured to estimate the time shift of the activity time zone of the first subject based on a detection value of a position sensor which detects a position of the first subject.

8. The device according to claim 1, wherein
the biomedical signal is a signal having the biological rhythm of a circadian rhythm, and
the CPU is further configured to set the first calculation period to a time period based on a first reference time set to a first time 6 hours prior to a peak time in the first physiological index time series data and a second reference time set to a second time 6 hours subsequent to the peak time.

9. The device according to claim 1, wherein the biomedical signal indicates a value of a core temperature.

10. The device according to claim 1, wherein
the biomedical signal indicates a pulse wave, and
the physiological index is one of a pulse rate or an augmentation index (AI) value.

11. The device according to claim 1, wherein the CPU is further configured to calculate, as the first calculation period, a period having a time length which is a half of a cycle with which the first physiological index time series data fluctuates.

12. The device according to claim 1, wherein the CPU is further configured to transmit the first phase shift amount and the average amplitude value of the first physiological index time series data to the server.

13. The device according to claim 1, wherein the CPU is further configured to display, on the display screen, the disturbance degree in a graphical format.

14. A biological rhythm disturbance degree calculating system, comprising:
a user device including a display screen and a first central processing unit (CPU),
wherein the first CPU is configured to:
receive estimation conditions including:
a time shift of an activity time zone of a subject of a plurality of subjects, and
a cause of the time shift of the activity time zone, wherein the cause of the time shift is one of an eastward travel across first zones with a first time difference or a westward travel across second zones with a second time difference, and
transmit the estimation conditions to a server; and
the server including a second CPU configured to:
acquire history information of the subject of the plurality of subjects based on the estimation conditions, wherein
first physiological index time series data of a physiological index and second physiological index time series data of the physiological index are acquired by the user device,
the acquisition of the first physiological index time series data and the second physiological index time series data is based on a biomedical signal of the subject acquired by a plurality of sensors,
the first physiological index time series data of the subject is based on the biomedical signal of the subject measured during a first time duration, and the second physiological index time series data of the subject is based on the biomedical signal of the subject measured during a second time duration;

set, based on the eastward travel and the history information, an average value of a first phase shift amount and a second phase shift amount, as a disturbance degree of a biological rhythm of the subject;

set, based on the westward travel and the history information, one of the first phase shift amount or the second phase shift amount, as the disturbance degree of the biological rhythm, wherein the first phase shift amount is calculated between the second physiological index time series data and the first physiological index time series data, in a first calculation period, the second phase shift amount is calculated between the second physiological index time series data and the first physiological index time series data, in a second calculation period, the first calculation period and the second calculation period are determined based on the first physiological index time series data of the subject, the first phase shift amount is calculated in the first calculation period based on a first ratio between a first feature quantity, and a sum of the first feature quantity and a second feature quantity, the second phase shift amount is calculated in the second calculation period based on a second ratio between the second feature quantity, and the sum of the first feature quantity and the second feature quantity, the first feature quantity corresponds to a first value of the second physiological index time series data of the subject, the first value of the second physiological index time series data of the subject is calculated using amplitudes of the second physiological index time series data that are larger than an average amplitude value of the first physiological index time series data, the second feature quantity corresponds to a second value of the second physiological index time series data of the subject, and the second value of the second physiological index time series data of the subject is calculated using amplitudes of the second physiological index time series data that are smaller than the average amplitude value of the first physiological index time series data;

generate information that indicates a recovery rate, the disturbance degree of the biological rhythm, and a recovery time of the subject, wherein the recovery rate is based on the estimation conditions; and transmit the information that indicates the recovery rate, the disturbance degree, and the recovery time to the user device, wherein the first CPU is further configured to control the display screen to display the information that indicates the recovery rate, the disturbance degree, and the recovery time of the subject.

15. A biological rhythm disturbance degree calculating method, comprising:

acquiring estimation conditions including:
a time shift of an activity time zone of a subject of a plurality of subjects, and
a cause of the time shift of the activity time zone, wherein the cause of the time shift is one of an eastward travel across first zones with a first time difference or a westward travel across second zones with a second time difference;

transmitting the estimation conditions to a server;

acquiring, from the server, history information of the subject of the plurality of subjects based on the estimation conditions;

acquiring first physiological index time series data of a physiological index and second physiological index time series data of the physiological index, wherein
the acquisition of the first physiological index time series data and the second physiological index time series data is based on a biomedical signal of the subject acquired by a plurality of sensors,
the first physiological index time series data of the subject is based on the biomedical signal measured during a first time duration, and
the second physiological index time series data of the subject is based on the biomedical signal measured during a second time duration;

determining a first calculation period and a second calculation period based on the first physiological index time series data;

calculating, in the first calculation period, a first phase shift amount between the second physiological index time series data and the first physiological index time series data, the first phase shift amount is calculated based on a first ratio between a first feature quantity, and a sum of the first feature quantity and a second feature quantity, wherein
the first feature quantity corresponds to a first value of the second physiological index time series data,
the first value of the second physiological index time series data is calculated using amplitudes of the second physiological index time series data that are larger than an average amplitude value of the first physiological index time series data,
the second feature quantity corresponds to a second value of the second physiological index time series data, and
the second value of the second physiological index time series data is calculated using amplitudes of the second physiological index time series data that are smaller than the average amplitude value of the first physiological index time series data;

calculating, in the second calculation period, a second phase shift amount between the second physiological index time series data and the first physiological index time series data, wherein the second phase shift amount is calculated based on a second ratio between the second feature quantity, and the sum of the first feature quantity and the second feature quantity;

setting, based on the eastward travel and the history information, an average value of the first phase shift amount and the second phase shift amount, as a disturbance degree of a biological rhythm of the subject;

setting, based on the westward travel and the history information, one of the first phase shift amount or the second phase shift amount, as the disturbance degree of the biological rhythm;

generating information that indicates a recovery rate, the disturbance degree of the biological rhythm, and a recovery time of the subject, wherein the recovery rate is based on the estimation conditions; and controlling a display screen to display the information that indicates the recovery rate, the disturbance degree, and the recovery time of the subject.

16. A non-transitory computer-readable storage medium having stored thereon computer-executable instructions that, when executed by a computer, cause the computer to execute operations, the operations comprising:
- acquiring estimation conditions including:
  - a time shift of an activity time zone of a subject of a plurality of subjects, and
  - a cause of the time shift of the activity time zone, wherein the cause of the time shift is one of an eastward travel across first zones with a first time difference or a westward travel across second zones with a second time difference;
- transmitting the estimation conditions to a server;
- acquiring, from the server, history information of the subject of the plurality of subjects based on the estimation conditions;
- acquiring first physiological index time series data of a physiological index and second physiological index time series data of the physiological index, wherein
  - the acquisition of the first physiological index time series data and the second physiological index time series data is based on a biomedical signal of the subject acquired by a plurality of sensors,
  - the first physiological index time series data of the subject is based on the biomedical signal measured during a first time duration, and
  - the second physiological index time series data of the subject is based on the biomedical signal measured during a second time duration;
- determining a first calculation period and a second calculation period based on the first physiological index time series data;
- calculating, in the first calculation period, a first phase shift amount between the second physiological index time series data and the first physiological index time series data, the first phase shift amount is calculated based on a first ratio between a first feature quantity, and a sum of the first feature quantity and a second feature quantity, wherein
  - the first feature quantity corresponds to a first value of the second physiological index time series data,
  - the first value of the second physiological index time series data is calculated using amplitudes of the second physiological index time series data that are larger than an average amplitude value of the first physiological index time series data,
  - the second feature quantity corresponds to a second value of the second physiological index time series data, and the second value of the second physiological index time series data is calculated using amplitudes of the second physiological index time series data that are smaller than the average amplitude value of the first physiological index time series data;
- calculating, in the second calculation period, a second phase shift amount between the second physiological index time series data and the first physiological index time series data, wherein the second phase shift amount is calculated based on a second ratio between the second feature quantity, and the sum of the first feature quantity and the second feature quantity;
- setting, based on the eastward travel and the history information, an average value of the first phase shift amount and the second phase shift amount, as a disturbance degree of a biological rhythm of the subject;
- setting, based on the westward travel and the history information, one of the first phase shift amount or the second phase shift amount, as the disturbance degree of the biological rhythm;
- generating information that indicates a recovery rate, the disturbance degree of the biological rhythm, and a recovery time of the subject, wherein the recovery rate is based on the estimation conditions; and
- controlling a display screen to display the information that indicates the recovery rate, the disturbance degree, and the recovery time of the subject.

* * * * *